(12) United States Patent
Roberts

(10) Patent No.: US 8,530,653 B2
(45) Date of Patent: Sep. 10, 2013

(54) ENZYME INHIBITING COMPOUNDS

(75) Inventor: Michael J. Roberts, Charlotte, NC (US)

(73) Assignee: Chelsea Therapeutics, Inc., Charlotte, NC (US)

( * ) Notice: Subject to any disclaimer, the term of this patent is extended or adjusted under 35 U.S.C. 154(b) by 344 days.

(21) Appl. No.: 12/939,556

(22) Filed: Nov. 4, 2010

(65) Prior Publication Data

US 2011/0112126 A1    May 12, 2011

Related U.S. Application Data

(60) Provisional application No. 61/258,763, filed on Nov. 6, 2009.

(51) Int. Cl.
| | | |
|---|---|---|
| C07D 239/72 | (2006.01) | |
| C07D 487/00 | (2006.01) | |
| A01N 43/54 | (2006.01) | |
| A01N 43/90 | (2006.01) | |

(52) U.S. Cl.
USPC ...... 544/291; 544/280; 514/266.4; 514/265.1

(58) Field of Classification Search
None
See application file for complete search history.

(56) References Cited

U.S. PATENT DOCUMENTS

| | | | |
|---|---|---|---|
| 4,818,753 A | 4/1989 | Colwell et al. | |
| 4,923,861 A | 5/1990 | Picard et al. | |
| 4,996,206 A | 2/1991 | Taylor et al. | |
| 4,996,207 A | 2/1991 | Nair et al. | |
| 5,028,608 A | 7/1991 | Taylor et al. | |
| 5,073,554 A | 12/1991 | Nair | |
| 5,106,974 A | 4/1992 | Akimoto et al. | |
| 5,196,424 A * | 3/1993 | Gossett et al. ............. | 514/265.1 |
| 5,248,775 A | 9/1993 | Taylor et al. | |
| 5,344,932 A | 9/1994 | Taylor | |
| 5,534,518 A | 7/1996 | Henrie, II et al. | |
| 5,550,128 A | 8/1996 | Nair et al. | |
| 5,593,999 A | 1/1997 | Nair et al. | |
| 5,866,580 A | 2/1999 | Gangjee | |
| 5,912,251 A | 6/1999 | Nair | |
| 5,955,100 A | 9/1999 | Bosslet et al. | |
| 6,048,736 A | 4/2000 | Kosak | |
| 6,146,658 A | 11/2000 | Bosslet et al. | |
| 6,667,318 B2 | 12/2003 | Burdick et al. | |
| 7,060,825 B2 | 6/2006 | Wu et al. | |
| 7,612,071 B2 | 11/2009 | Kamen et al. | |
| 2001/0034333 A1 | 10/2001 | Kosak | |
| 2002/0077280 A1 | 6/2002 | Judice et al. | |
| 2002/0081455 A1 | 6/2002 | Lee | |
| 2003/0162721 A1 | 8/2003 | Mehlem | |
| 2003/0181635 A1 | 9/2003 | Kochat et al. | |
| 2004/0092739 A1 | 5/2004 | Xiao et al. | |
| 2005/0020833 A1 | 1/2005 | Wu et al. | |
| 2005/0154042 A1 | 7/2005 | Bratton et al. | |
| 2006/0111272 A1 | 5/2006 | Roberts et al. | |
| 2006/0111413 A1 | 5/2006 | Sher et al. | |
| 2006/0142315 A1 | 6/2006 | Rosowsky et al. | |
| 2006/0160751 A1 | 7/2006 | McGuire | |
| 2007/0265444 A1 | 11/2007 | Stoicescu | |
| 2008/0207652 A1 | 8/2008 | Stoicescu | |
| 2008/0214550 A1 | 9/2008 | Stoicescu | |
| 2009/0253719 A1 | 10/2009 | Pimplaskar et al. | |
| 2009/0253720 A1 | 10/2009 | Roberts et al. | |
| 2010/0249141 A1 | 9/2010 | Stoicescu | |

FOREIGN PATENT DOCUMENTS

| | | |
|---|---|---|
| DE | 4236237 | 4/1994 |
| EP | 0 239 362 | 9/1987 |
| EP | 0 340 905 | 11/1989 |
| EP | 1 754 484 A1 | 2/2007 |
| WO | WO 93/13079 | 7/1993 |
| WO | WO 02/081455 A1 | 10/2002 |
| WO | WO 2005/097134 A2 | 10/2005 |
| WO | WO 2006/087630 | 8/2006 |

OTHER PUBLICATIONS

Caira, "Crystalline Polymorphism of Organic Compounds," *Topics in Current Chemistry*, 1998, pp. 163-208, vol. 198.

Morissette et al., "High-Throughput Crystallization: Polymorphs, Salts, Co-Crystals and Solvates of Pharmaceutical Solids," *Advance Drug Delivery Reviews*, 2004, pp. 275-300, vol. 56.

Pauwels et al. "Burden and Clinical Features of Chronic Obstructive Pulmonary Disease (COPD)," *R A. Lancet* (2004) 364(9434):613-20).

Wang et al. Review of Excipients and pH's for Parenteral Products Used in the United States, (1980) *J. Parent. Drug Assn.* 34(6):452-462.

West, "Solid State Chemistry and its Applications," Wiley, New York, 1988, pp. 358 and 365.

Abraham et al., "Folate Analogues. 34. Synthesis and Antitumor Activity of Non-Polyglutamylatable Inhibitors of Dihydrofolate Reductase," *J. Med. Chem.*, 1991, vol. 34, pp. 222-227.

Abraham et al., "Aldehyde Oxidase Mediated 7-Hydroxylation of Antifolates and Its Therapeutic Relevance," *Cellular Pharmacology*, 1996, vol. 3, pp. 29-34.

Alarcon et al., "Controlled Trial of Methotrexate Versus 10-Deazaaminopterin in the Treatment of Rheumatoid Arthristis," *Arthritis Rheumatism*, 1992, pp. 600-660, vol. 51, No. 5.

Amato et al., "Metabolism-Based Antifolate Drug Design: MDAM and MTREX," *Pharmacology and Therapeutics in the New Millennium*, 2001, pp. 204-212, Narosa Publishing House, New Delhi, India.

Baggott et al., "Folylpoly-γ-glutamates as Cosubstrates of 10-Formyltetrandrofolate:5'-Phosphoribosyl-5amino-4-imidazole-Carboxamide Formyltransferase," *Biochemistry*, 1979, pp. 1036-41, vol. 18, No. 1.

(Continued)

*Primary Examiner* — James O Wilson
*Assistant Examiner* — Oluwafemi Masha
(74) *Attorney, Agent, or Firm* — Womble Carlyle Sandridge & Rice, LLP

(57) ABSTRACT

The present invention is directed to compounds that are specifically structured to provide enzyme inhibition. In specific embodiments, the enzyme inhibiting compounds exhibit antifolate activity. Particularly, the inventive compounds are formed of an antifolate residue that is active in inhibiting one or more of TS, DHFR, GAR, FPGS, and AICAR Tfase. The enzyme inhibiting compounds are useful in a variety of methods of treatment, including treating abnormal cell proliferation and treating inflammation.

6 Claims, 6 Drawing Sheets

(56) References Cited

OTHER PUBLICATIONS

Baugh et al., "Polygammaglutamyl Metabolites of Methotrexate," *Biochemical and Biophysical Research Communications*, 1973, pp. 27-34, vol. 52, No. 1.

Blakley, *The Biochemistry of Folic Acid and Related Pteridines*. 1969, Amsterdam Elsevier. [Book].

Broxterman et al., "Cancer Research 2001: Drug Resistance, New Targets and Drug Combinations," *Drug Resistance Updates*, 2001, vol. 4, pp. 197-209.

Bryant et al., "Metabolism-Blocked Antifolate-2," *Proc. Am. Assoc. Cancer Res.*, 1999, vol. 40, p. 293 (Abstract No. 1944).

Caperelli et al., "The Human Glycinamide Ribonucleotide Transformylase Domain: Purification, Characterization and Kinetic Mechanism," *Archives of Biochemistry and Biophysics*, 1997, pp. 98-103, vol. 341, No. 1.

Castaneda et al., "Controlled Trial of Methotrexate Versus CH-1504 in the Treatment of Rheumatoid Arthritis," *Journal of Rheumatology* 2006, pp. 862-864, vol. 33, No. 1.

Choi et al., "Methotrexate and Mortality in Patients with Rheumatoid Arthritis: A Prospective Study", *The Lancet*, 2002, pp. 1173-1177, vol. 359.

Clowes et al., "Prevention of Stenosis After Vascular Reconstruction: Pharmacologic Control of Intimal Hyperplasia—A Review," *Journal of Vascular Surgery*, 1991, pp. 885-890, vol. 13.

Degraw et al., "Synthesis and Antifolate Activity of 8,10-Dideazaminopterin," *J. Het. Chem.*, 1982, vol. 19, pp. 1587-1588.

Dessein et al., "Effects of Disease Modifying Agents and Dietary Intervention on Insulin Resistance and Dyslipidemia in Inflammatory Arthritis: A Pilot Study", *Arthritis Res*. 2002, pp. 1-7, vol. 4, No. 6.

Dolnick et al., "Human Thymidylate Synthetase Derived From Blast Cells of Patients With Acute Myelocytic Leukemia," *The Journal of Biological Chemistry*, 1977, pp. 7697-7703, vol. 252, No. 1.

Gahtan et al., "Inflammatory Pathogenesis in Alzheimer's Disease: Biological Mechanisms and Cognitive Sequeli," *Neuroscience and Biobehavioral Reviews*, 1999, pp. 615-633, vol. 23, No. 5.

Gangjee et al., "Nonclassical 2,4-Diamino-8-Deazafolate Analogues as Inhibitors of Dihydrofolate Reductases from Rat Liver, *Pneumocystis carinii*, and *Toxoplasma gondii*," *J Med. Chem.*, 1996, vol. 39(9), pp. 1836-1845.

Gangjee et al., "Effect of N-9-Methylation and Bridge Atom Variation on the Activity of 5-Substituted 2, 4-Diaminopyrrolo (2,3-d) Pyrimidines Against Dihydrofolate Reductases From *Pneumocystis carinii* and *Toxoplasma gondii*," *Journal of Medicinal Chemistry*, 1997, pp. 1173-1177, vol. 40, No. 7.

Gangjee et al., "Design, Synthesis, and Biological Activities of Classical N-{4-[2-(2-Amino-4-ethylpyrrolo[2,3-*d*]pyrimidin-5-yl)ethyl]benzoyl}-L-glutamic Acid and Its 6-Methyl Derivative as Potential Dual Inhibitors of Thymidylate Synthase and Dihydrofolate Reductase and as Potential Antitumor Agents," *J. Med. Chem..*, 2003, pp. 591-600, vol. 46, No. 4.

Grant Proposal, "Mobiletrex (M-Trex) for the Prevention and/or Treatment of Coronary Heart Disease", American Heart Association, Jan. 23, 2003, 35 pages.

Grant Application, "Anti-inflammatory Antifolate Therapy for Heart Disease", Department of Health and Human Services, Jan. 23, 2003, 27 pages.

Gupta et al., "Inflammation and Alzheimer's Disease," *The International Journal of Clinical Practice*, 2003, pp. 36-39, vol. 57, No. 1.

Itoh et al., "Non-Glutamate Type Pyrrolo[2,2-*d*]pyrimidine Antifolates. II. Synthesis and Antitumor Activity of N-Substituted Glutamine Analogs," *Chemical and Pharmaceutical Bulletin, Pharmaceutical Society of Japan*, 1996, pp. 1498-1509, vol. 44, No. 8.

Jackman, "Antifolate Drugs in Cancer Therapy," *Book Review: Reprints from Current Trends, Drug Discovery Today*, 1999.

Johns et al., "Enzymic Oxidation of Methotrexiate and Aminopterin," *Life Sciences*, 1964, pp. 1383-1388, vol. 3.

Johns et al.,"Metabolism of Folate Antagonists," *Annals New York Academy of Sciences*, 1971, pp. 378-386, vol. 186.

Kisliuk, "Deaza Analogs of Folic Acid as Antitumor Agents," *Current Pharmaceutical Design*, 2003, vol. 9(31), pp. 2615-2625.

Kormeili et al., Psoriasis: Immunopathogenesis and Evolving Immunomodulators and Systemic Therapies; U.S. Experiences, *British Journal of Dermatology*, 2004, pp. 3-15, vol. 151, No. 1.

Lemanske, "Inflammation in Childhood Asthma and Other Wheezing Disorders," *Pediatrics*, 2002, pp. 368-372, vol. 109, No. 2.

Lim, et al., "Gene-Nutrient Interactions Among Determinants of Folate and One-Carbon Metabolism on the Risk of Non-Hodgkin Lymphoma: NCI-SEER Case-Control Study," *Blood*, 2007, pp. 3050-3059, vol. 109, No. 7.

Lind, "Circulating Markers of Inflammation and Atherosclerosis," *Atherosclerosis*, 2003, pp. 203-214, vol. 169, No. 2.

Lloyd et al., "Crystallization and Preliminary Crystallographic Analysis of Carboxypeptidase $G_2$ From *Pseudomonas* sp. Strain RS-16," *J. Mol. Biol.*, 1991, pp. 17-18, vol. 220.

Matherly et al., "Membrane Transport of Folates," *Vitam Horm*, 2003, pp. 403-456, vol. 66. [Abstract].

McCullough et al., "Purification and Properties of Carboxypeptidase G" *The Journal of Biological Chemistry*, 1971, pp. 7201-7213, vol. 246, No. 23.

McGuire et al., "Enzymatic Synthesis of Polyglutamate Derivatives of 7-Hydroxymethotrexatel," *Biochemical Pharmacology*, 1984, pp. 1355-1361, vol. 33, No. 8.

McGuire et al., "Biochemical and Growth Inhibitory Effects of the *erythro* and *threo* Isomers of γ-Fluoromethotrexate, a Methotrexate Analogue Defective in Polyglutamylation," *Cancer Research*, 1989, pp. 4517-4525, vol. 49, No. 12.

McGuire et al., "Biochemical and Growth Inhibition Studies of Methotrexate and Aminopterin Analogues Containing a Tetrazole Ring in Place of the γCarboxyl Group," *Cancer Research*, 1990, pp. 1726-1731, vol. 50.

McGuire et al., "Biochemical and Biological Properties of Methotrexate Analogs Containing D-glutamic Acid or D-erythro,threo-4-fluoroglutamic Acid," *Biochemical Pharmacology*, 1991, pp. 2400-2403, vol. 42, No. 12.

McGuire et al., "Novel 6,5-fused Ring Heterocyclic Antifolates: Biochemical and Biological Characterization," *Cancer Research*, 1994, pp. 2673-2679, vol. 54.

McGuire, "Anticancer Antifolates: Current Status and Future Directions," *Current Pharmaceutical Design*, 2003, vol. 9(31), pp. 2593-2613.

McGuire et al., "5-Amino-4-Imidazolecarboxamide Riboside Potentiates Both Transport of Reduced Folates and Antifolates by the Human Reduced Folate Carrier and Their Subsequent Metabolism," *Cancer Research*, 2006, pp. 3836-3844, vol. 66, No. 7.

McGuire, et al., "Metabolism-blocked Antifolates as Potential Antirheumatoid Arthritis Agents: 4-Amino-4-deoxy-5,8,10-trideazapteroyl -D,L-4'-methyleneglutamic Acid (CH-1504) and Its Analogs," *Biochemical Pharmacology*, 2009, pp. 1161-1172, vol. 77, No. 7.

Merriam-Webster's Collegiate Dictionary, Merriam-Webster Incorporated: Springfield, Massachusetts, 1993, pp. 311 and 996.

Mirza et al., "The Absence of Reactive Astrocytosis in Indicative of a Unique Inflammatory Process in Parkinson's Disease," *Neuroscience*, 2000, pp. 425-432, vol. 95, No. 2.

Miwa et al., "A Novel Synthetic Approach to Pyrrolo(2,3-d)pyrimidine Antifolates," *Journal of Organic Chemistry*, 1993, pp. 1696-1701, vol. 58, No. 7.

Montgomery et al., "Design and Synthesis of Folate Analogs as Antimetabolites in Folate Antagonists as Therapeutic Agents," *Biochemistry, Molecular Actions and Synthetic Designs*, 1984, pp. 219-261, vol. 1.

Moran et al. "Relative Substrate Activities of Structurally Related Pteridine, Quinazoline, and Pyrimidine Analogs for Mouse Liver Folylpolyglutamate Synthetase," *Molecular Pharmacology*, 1989, pp. 736-743, vol. 36, No. 5.

Nagayama et al., "Eosinophils and Basophilic Cells in Sputum and Nasal Smears Taken from Infants and Young Children during Acute Asthma," *Pediatr. Allergy Immunol.*, 1995, vol. 6, pp. 204-208.

Nair et al., "Folate Analogues. 34. Synthesis and Antitumor Activity of Non-Polyglutamylatable Inhibitors of Dihydrofolate Reductase," *J. Med. Chem*, 1991, pp. 222-227, vol. 34.

Nair et al., "Polyglutamylation as a Determinant of Cytotoxicity of Classical Folate Analogue Inhibitors of Thymidylate Synthase and Glycinamide Ribonucleotide Formyltransferase," *Cellular Pharmacology*, 1994, vol. 1, pp. 245-249.

Nair et al., "Aldehyde Oxidase Mediated 7-Hydroxylation of Antifolates and its Therapeutic Relevance," *Cellular Pharmacology*, 1996, pp. 29-34, vol. 3.

Nair et al., "Metabolism-Blocked Antifolates-1," *Proc. Am. Assoc. Cancer Res.*, 1998, vol. 39, p. 431 (Abstract No. 2938).

Nair et al., "Metabolism Blocked Classical Folate Analog Inhibitors of Dihydrofolate Reductase-1: Synthesis and Biological Evaluation of Mobiletrex," *Medicinal Chemistry Research*, 1999, pp. 176-185, vol. 9, No. 3.

Nair et al., "Metabolism-Blocked Antifolates, 3: Enantiomers of 4'methylene-5,8,10-Trideazaaminopterin(M-Trex)," *Proceedings of the American Assoication for Cancer Research Annual Meeting*, 2001, pp. 294, vol. 42. (Abstract No. 1583).

Park et al., "Effects of Antirheumatic Therapy on Serum Lipid Levels in Patients with Rheumatoid Arthritis: A Prospective Study", *Am. J Med.*, 2002, pp. 188-193, vol. 113, No. 3.

Renouard et al., "Functionalized Tetradentate Ligands for Ru-Sensitized Solar Cells," *Tetrahedron*, 2001, vol. 57, pp. 8145-8150.

Rosowsky et al., "Analogues of Methotrexate and Aminopterin with γ-Methylene and γ-Cyano Substitution of the Glutamate Side Chain: Synthesis and in Vitro Biological Activity," *J. Med. Chem.*, 1991, vol. 34, pp. 203-208.

Ross, "Atherosclerosis—An Inflammatory Disease," *New England Journal of Medicine*, 1999, pp. 115-126, vol. 340.

Sherwood et al., "Purification and Properties of Carboxypeptidase G2 From *Pseudomonas* sp. Strain RS-16," *Eur. J Biochem.*, 1985, pp. 447-453, vol. 148.

Shilai et al., "Selective Metallation of Thiophene and Thiazole Rings with Magnesium Amide Base," *J. Chem. Soc., Perkin Trans. 1*, 2001, pp. 442-444.

Takimoto, "New Antifolates: Pharmacology and Clinical Applications," *The Oncologist*, 1996, pp. 68-81, vol. 1.

Van Triest et al., "Downstream Molecular Determinants of Response to 5-Fluorouracil and Antifolate Thymidylate Synthase Inhibitors," *Annals of Oncology*, 2000, pp. 385-391, vol. 11.

Yan et al., "Folic Acid Analogs . III. N-(2-[2-(,4-diamino-6-quinazolinyl)ethyl] benzoyl)-L-glutamic acid," *J. Heterocyclic Chem.*, 1979, 541-544, vol. 16.

Chan et al., "Design, Synthesis, and Antifolate Activity of New Analogues of Piritrexim and Other Diaminopyrimidine Dihydrofolate Reductase Inhibitors with ω-Carboxyalkoxy or ω-Carboxy-1-alkynyl Substitution in the Side Chain," *J. Med. Chem.* 2005, vol. 48, pp. 4420-4431.

Nair et al., "Folate Analogues. 20. Synthesis and Antifolate Activity of 1',2',3',4',5',6'-Hexahydrohomofolic Acid," *J.Med.Chem.*, 1983, vol. 26, pp. 135-140.

Rosowsky et al., "Methotrexate Analogs. 7. Synthesis of Two Higher Homologs and a Positional Isomer of Methotrexate Diethyl Ester as Potential Antitumor Agents," *J. Heterocyclic Chem.*, 1976, vol. 13, 727-732.

Sliskovic et al., "Inhibitors of Cholesterol Biosynthesis. 4. Trans-6-[2-(Substituted-quinolinyl)ethenyl/ethyl]tetrahydro-4-hydroxy-2H-pyran-2-ones, a Novel Series of HMG-CoA Reductase Inhibitors," *J. Med. Chem.*, 1991, vol. 34, pp. 367-373.

Yamini et al., "Inhibitors of Human Dihydrofolate Reductase: A Computational Design and Docking Studies Using Glide," *E-Journal of Chemistry*, 2008, vol. 5, No. 2. www.e-journals.net.

\* cited by examiner

ENZYME INHIBITING COMPOUNDS

CROSS-REFERENCE TO RELATED APPLICATIONS

The present application claims priority to U.S. Provisional Patent Application No. 61/258,763, filed Nov. 6, 2009, the entire disclosure of which is incorporated herein by reference in its entirety.

FIELD OF THE INVENTION

The present invention is directed to compounds having enzyme inhibition activity. In particular, the invention is directed to compounds that inhibit at least one enzyme related to folate metabolism and thus exhibit antifolate activity.

BACKGROUND

Enzymes are biomolecules (typically proteins) that catalyze chemical reaction. In fact, enzymes are known to play a part in literally thousands of biochemical reactions. Enzymes generally function by action on a specific substrate to form a specific product, and the underlying reactions are dramatically hindered or completely impossible in the absence or inhibition of the necessary enzyme. Enzyme inhibitors are compounds or molecules that interact with enzymes in some fashion so as to inhibit the normal activity of the enzyme. For example, the binding of an inhibitor can stop a substrate from entering the active site of the enzyme and/or hinder the enzyme from catalyzing its specific reaction. The level of inhibition can vary from a mild decrease in effectiveness of the enzyme to a complete ceasing of enzyme function. Given the broad activity of various enzymes in living organisms, it is not surprising that many enzyme inhibitors have been developed for pharmaceutical applications. Medicinal enzyme inhibitors are often judged based on specificity (i.e., lack of binding to other proteins) and potency (i.e., the dissociation constant, which indicates the concentration needed to inhibit the specified enzyme). High specificity and potency are desired to limit drug side effects and ensure low toxicity.

One group of enzyme inhibitors that has shown great usefulness is the so-called "antifolates". Folic acid is a water-soluble B vitamin known by the systematic name N-[4(2-amino-4-hydroxy-pteridin-6-ylmethylamino)-benzoyl]-L (+)-glutamic acid and having the structure provided below in Formula (1).

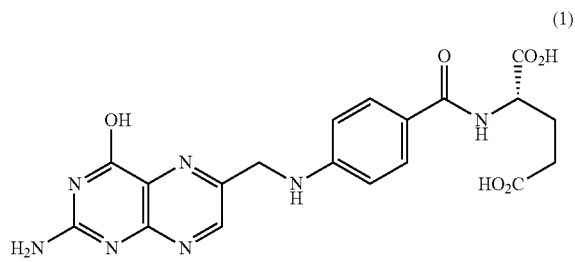 [SMILES: Nc1nc(O)c2nc(CNc3ccc(C(=O)N[C@@H](CCC(=O)O)C(=O)O)cc3)cnc2n1]

(1)

As seen in Formula (1), the folic acid structure can generally be described as being formed of a pteridine ring, a para-aminobenzoic acid moiety, and a glutamate moiety. Folic acid and its derivatives are necessary for metabolism and growth, particularly participating in the body's synthesis of thymidylate, amino acids, and purines. Derivatives of folic acid, such as naturally occurring folates, are known to have biochemical effects comparable to folic acid. Folic acid itself is derivatized via hydrogenation, such as at the 1,4-diazine ring, or being methylated, formaldehydylated, or bridged, wherein substitution is generally at the $N^5$ or $N^{10}$ positions. Folates have been studied for efficacy in various uses including reduction in severity or incidence of birth defects, heart disease, stroke, memory loss, and age-related dementia.

Antifolate compounds are structurally similar to folic acid and function to disrupt folic acid metabolism. A review of antifolates is provided by Takamoto (1996) The Oncologist, 1:68-81, which is incorporated herein by reference. One specific group of antifolates, the so-called "classical antifolates," is characterized by the presence of a folic acid p-aminobenzoylglutamic acid side chain, or a derivative of that side chain. Another group of antifolates, the so-called "nonclassical antifolates," are characterized by the specific absence of the p-aminobenzoylglutamic group. Because antifolates have a physiological effect that is opposite the effect of folic acid, antifolates have been shown to exhibit useful physiological functions, such as the ability to destroy cancer cells by causing apoptosis.

An intact folate enzyme pathway is important to maintain de novo synthesis of the building blocks of DNA, as well as many important amino acids. Antifolate targets include the various enzymes involved in folate metabolism, including (i) dihydrofolate reductase (DHFR); (ii) thymidylate synthase (TS); (iii) folylpolyglutamyl synthase (FPGS); (iv) glycinamide ribonucleotide formyltransferase (GAR); and (v) aminoimidazole carboxamide ribonucleotide transformylase (AICAR Tfase).

The reduced folate carrier (RFC), which is a transmembrane glycoprotein, plays an active role in the folate pathway transporting reduced folate into mammalian cells via the carrier mediated mechanism (as opposed to the receptor mediated mechanism). The RFC also transports antifolates, such as methotrexate. Thus, mediating the ability of RFC to function can affect the ability of cells to uptake reduced folates.

Further folic acid derivatives have also been studied in the search for antifolates with increased metabolic stability allowing for smaller doses and less frequent patient administration. For example, a dideaza (i.e., quinazoline-based) analog has been shown to avoid physiological hydroxylation on the pteridine ring system. Furthermore, replacement of the secondary amine nitrogen atom with an optionally substituted carbon atom has been shown to protect neighboring bonds from physiological cleavage.

The multiple enzymes involved in folic acid metabolism within the body present a choice of inhibition targets for antifolates. In other words, it is possible for antifolates to vary as to which enzyme(s) they inhibit. For example, some antifolates inhibit primarily DHFR, while other antifolates inhibit primarily TS, GAR, FPGS, or AICAR Tfase, while still other antifolates inhibit combinations of these enzymes.

Given the usefulness of enzyme inhibiting compounds in treating various conditions and diseases, it would be beneficial to have new compounds exhibiting such enzyme inhibition. The present invention meets this need.

SUMMARY OF THE INVENTION

The present invention provides enzyme inhibiting compounds that particularly may inhibit enzyme activity typically associated with antifolates (e.g., inhibiting of one or more of TS, DHFR, GAR, FPGS, and AICAR Tfase). These compounds, and pharmaceutical formulations thereof, that can particularly provide excellent anti-inflammatory properties, as well as further uses, are described herein.

Accordingly, in one aspect, the present invention provides an enzyme inhibiting compound. In particular embodiments, a compound according to the invention comprises a segment imparting antifolate activity.

In some embodiments, the invention provides an enzyme inhibiting compound according to the structure of Formula (13)

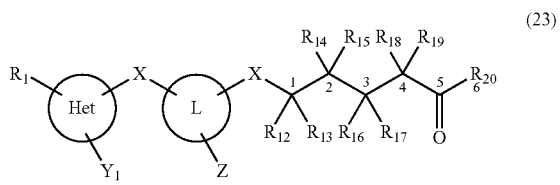

(23)

wherein:

Het is an optionally aromatic fused ring structure formed of two fused six-membered rings or a six-membered ring fused with a five-membered ring, one or both of the fused rings comprising up to 3 heteroatoms selected from the group consisting of O, S, and N, and each ring structure may comprise one or more substituents $R_1$ and $Y_1$, as described below, attached to any ring carbon atom or heteroatom;

$Y_1$ is selected from the group consisting of H, optionally substituted alkyl, optionally substituted alkenyl, optionally substituted alkynyl, carbonyl, optionally substituted alkoxy, hydroxyl, nitro, halo, optionally substituted acyl, —C(O)-alkyl, —C(O)-alkenyl, —C(O)-alkynyl; and $NR_4R_5$;

$R_1$ is selected from the group consisting of H, optionally substituted alkyl, optionally substituted alkenyl, optionally substituted alkynyl, optionally substituted acyl, —C(O)-alkyl, —C(O)-alkenyl, and —C(O)-alkynyl;

$R_4$ and $R_5$ are independently selected from the group consisting of H, optionally substituted alkyl, optionally substituted alkenyl, optionally substituted alkynyl, optionally substituted acyl, —C(O)-alkyl, —C(O)-alkenyl, and —C(O)-alkynyl;

X is a group selected from amino, amide, oxygen, or alkylene, wherein the alkylene optionally includes one or more heteroatoms, and wherein one or more of any carbon or nitrogen atoms is optionally substituted with one or more substituents $R_9$;

$R_9$ is selected from the group consisting of H, optionally substituted alkyl, optionally substituted alkenyl, optionally substituted alkynyl, O, optionally substituted acyl, —C(O)-alkyl, —C(O)-alkenyl, —C(O)-alkynyl, optionally substituted alkoxy, hydroxyl, and halo;

L is optional and is an aliphatic group or an aromatic or non-aromatic ring structure comprising 5-20 ring atoms;

Z is one or more substituents and is selected from the group consisting of H, halo, optionally substituted alkyl, optionally substituted, hydroxyl, carbonyl, $CF_3$, optionally substituted alkenyl, optionally substituted alkynyl, optionally substituted aryl, alkaryl, arylalkyl, optionally substituted heteroaryl, optionally substituted heterocycle, amino, alkylamino, dialkylamino, carboxylic acid, carboxylic ester, carboxamide, nitro, cyano, amide, imide, azide, alkylcarbonyl, optionally substituted acyl, sulfonyl, alkylsulfonyl, sulfinyl, alkylsulfinyl, sulfenyl, alkylsulfenyl, and trialkylammonium;

$R_{12}$, $R_{13}$, $R_{14}$, $R_{15}$, $R_{16}$, $R_{17}$, $R_{18}$, $R_{19}$, and $R_{20}$ are independently selected from the group consisting of H, hydroxyl, optionally substituted alkyl, optionally substituted alkoxy, halo, optionally substituted acyl, and —C(O)-alkyl;

the labeled atoms 1 through 6 may be cyclized forming a six-membered ring, optionally including one or more O ring atoms; and pharmaceutically acceptable esters, amides, salts, solvates, prodrugs, and enantiomers thereof.

In further embodiments, the invention provides an enzyme inhibiting compound according to the structure of Formula (14)

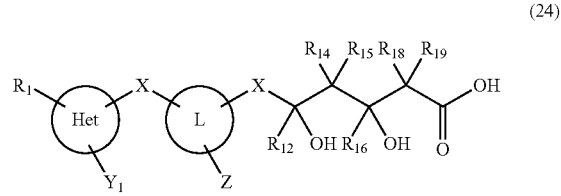

(24)

wherein the substituent groups are as defined in relation to the structure of Formula (13).

In other embodiments, the invention provides enzyme inhibiting compounds according to the structures of Formula (13) and Formula (14) wherein the ring Het is any one of the structures provides in Formula (15) through Formula (18)

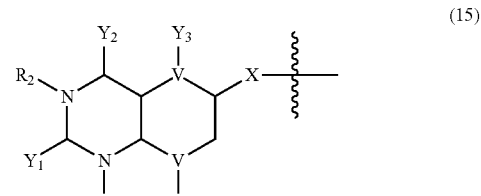

(15)

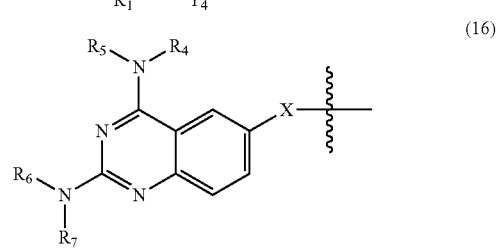

(16)

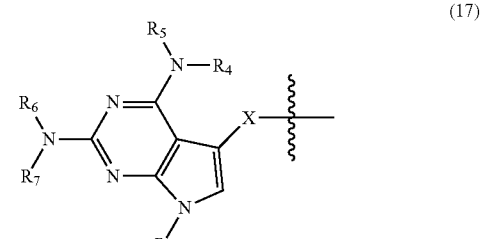

(17)

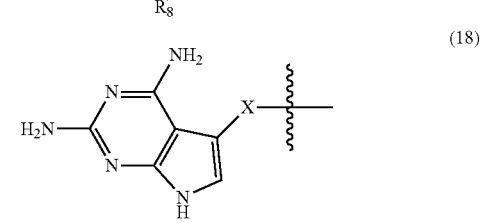

(18)

wherein:

the two six-membered ring fused system of Formula (15) is optionally aromatic;

$Y_1$ and $Y_2$ are independently selected from the group consisting of H, optionally substituted alkyl, optionally substituted alkenyl, optionally substituted alkynyl, carbonyl, optionally substituted alkoxy, hydroxyl, nitro, halo, optionally substituted acyl, —C(O)-alkyl, —C(O)-alkenyl, —C(O)-alkynyl; and $NR_4R_5$;

$R_1$, $R_2$, $Y_3$, and $Y_4$ are independently selected from the group consisting of H, optionally substituted alkyl, optionally substituted alkenyl, optionally substituted alkynyl, optionally substituted acyl, —C(O)-alkyl, —C(O)-alkenyl, and —C(O)-alkynyl;

each V is independently C, N, O, or S;

$R_4$, $R_5$, $R_6$, $R_7$, and $R_8$ are independently selected from the group consisting of H, optionally substituted alkyl, optionally substituted alkenyl, optionally substituted alkynyl, optionally substituted acyl, —C(O)-alkyl, —C(O)-alkenyl, and —C(O)-alkynyl;

X is a group selected from amino, amide, oxygen, or alkylene, wherein the alkylene optionally includes one or more heteroatoms, and wherein one or more of any carbon or nitrogen atoms of X is optionally substituted with one or more substituents $R_9$;

$R_9$ is selected from the group consisting of H, optionally substituted alkyl, optionally substituted alkenyl, optionally substituted alkynyl, O, optionally substituted acyl, —C(O)-alkyl, —C(O)-alkenyl, —C(O)-alkynyl, optionally substituted alkoxy, hydroxyl, and halo;

the wavy bond indicates the point of attachment to the remaining portion of the structure; and pharmaceutically acceptable esters, amides, salts, solvates, prodrugs, and enantiomers thereof.

In more specific embodiments, the invention provides an enzyme inhibiting compound according to according to any of the following structures

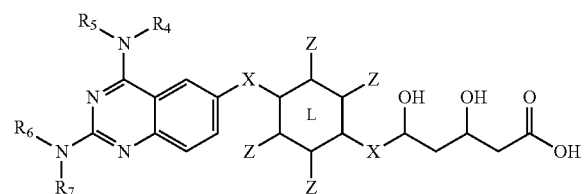

(19)

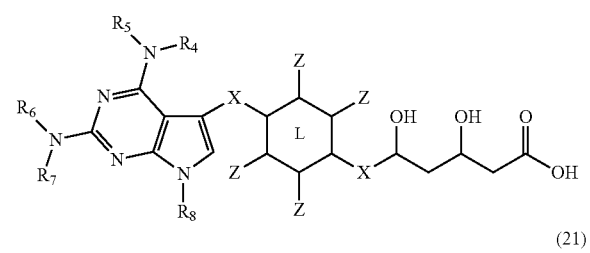

(20)

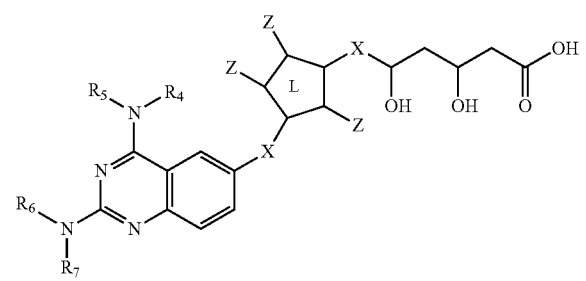

(21)

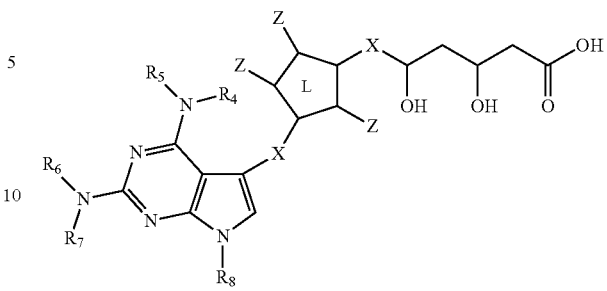

(22)

wherein, in each of Formula (19) through Formula (22):

$R_4$, $R_5$, $R_6$, $R_7$, and $R_8$ are independently selected from the group consisting of H, optionally substituted alkyl, optionally substituted alkenyl, optionally substituted alkynyl, optionally substituted acyl, —C(O)-alkyl, —C(O)-alkenyl, and —C(O)-alkynyl;

X is a group selected from amino, amide, oxygen, or alkylene, wherein the alkylene optionally includes one or more heteroatoms (e.g., N or O), and wherein one or more of any carbon or nitrogen atoms of X is optionally substituted with one or more substituents $R_9$;

$R_9$ is selected from the group consisting of H, optionally substituted alkyl, optionally substituted alkenyl, optionally substituted alkynyl, O, optionally substituted acyl, —C(O)-alkyl, —C(O)-alkenyl, —C(O)-alkynyl, optionally substituted alkoxy, hydroxyl, and halo;

ring structure "L" is optionally aromatic, and one or more ring carbons are optionally replaced with a heteroatom selected from N, O, or S;

each Z is independently selected from the group consisting of H, halo (i.e., chloro, bromo, iodo, or fluoro), optionally substituted alkyl, optionally substituted alkoxy, hydroxyl, carbonyl, $CF_3$, optionally substituted alkenyl, optionally substituted alkynyl, optionally substituted aryl, alkaryl, arylalkyl, optionally substituted heteroaryl, optionally substituted heterocycle, amino, alkylamino, dialkylamino, carboxylic acid, carboxylic ester, carboxamide, nitro, cyano, amide, imide, azide, alkylcarbonyl, optionally substituted acyl, sulfonyl, alkylsulfonyl, sulfinyl, alkylsulfinyl, sulfenyl, alkylsulfenyl, and trialkylammonium; and pharmaceutically acceptable esters, amides, salts, solvates, prodrugs, and enantiomers thereof.

In certain embodiments, the invention provides an enzyme inhibiting compound according to the following specific structures

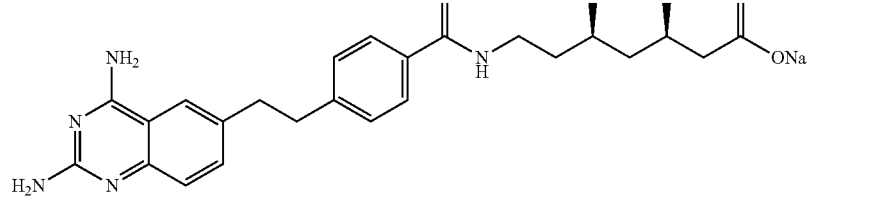

(23)

-continued

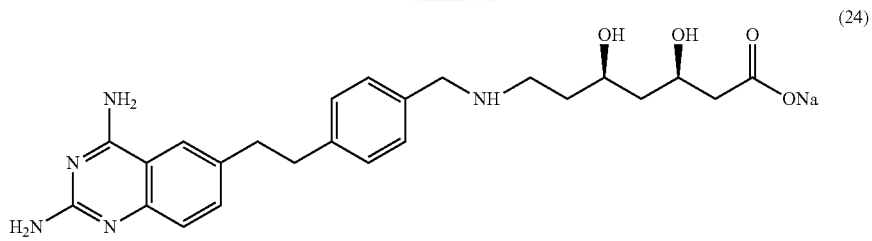

(24)

In another aspect, the invention also provides pharmaceutical compositions. In certain embodiments, a pharmaceutical composition according to the invention may comprise a pharmaceutically acceptable carrier and one or more enzyme inhibiting compounds as described herein.

In still another aspect, the invention provides various methods of treatment. In certain embodiments, the methods can comprise administering to a patient one or more enzyme inhibiting compounds as described herein. In specific embodiments, the method can comprise one or a combination of:

1) A method of inhibiting TS activity;
2) A method of inhibiting DHFR activity;
3) A method of inhibiting FPGS activity;
4) A method of inhibiting GAR activity;
5) A method of inhibiting AICAR Tfase activity;
6) A method of disrupting folic acid metabolism;
7) A method of treating abnormal cell proliferation;
8) A method of treating cancer;
9) A method of treating inflammation;
10) A method of treating inflammatory bowel disease;
11) A method of treating Crohn's disease;
12) A method of treating ulcerative colitis;
13) A method of treating arthritis;
14) A method of treating rheumatoid arthritis;
15) A method of treating osteoarthritis;
16) A method of treating an autoimmune inflammatory disease;
17) A method of treating system lupus erythematosus (SLE);
18) A method of treating psoriasis;
19) A method of treating psoriatic arthritis;
20) A method of treating uveitis;
21) A method of treating asthma;
22) A method of treating cardiovascular disease; or
23) A method of treating atherosclerosis.

BRIEF DESCRIPTION OF THE DRAWINGS

Figure 1:
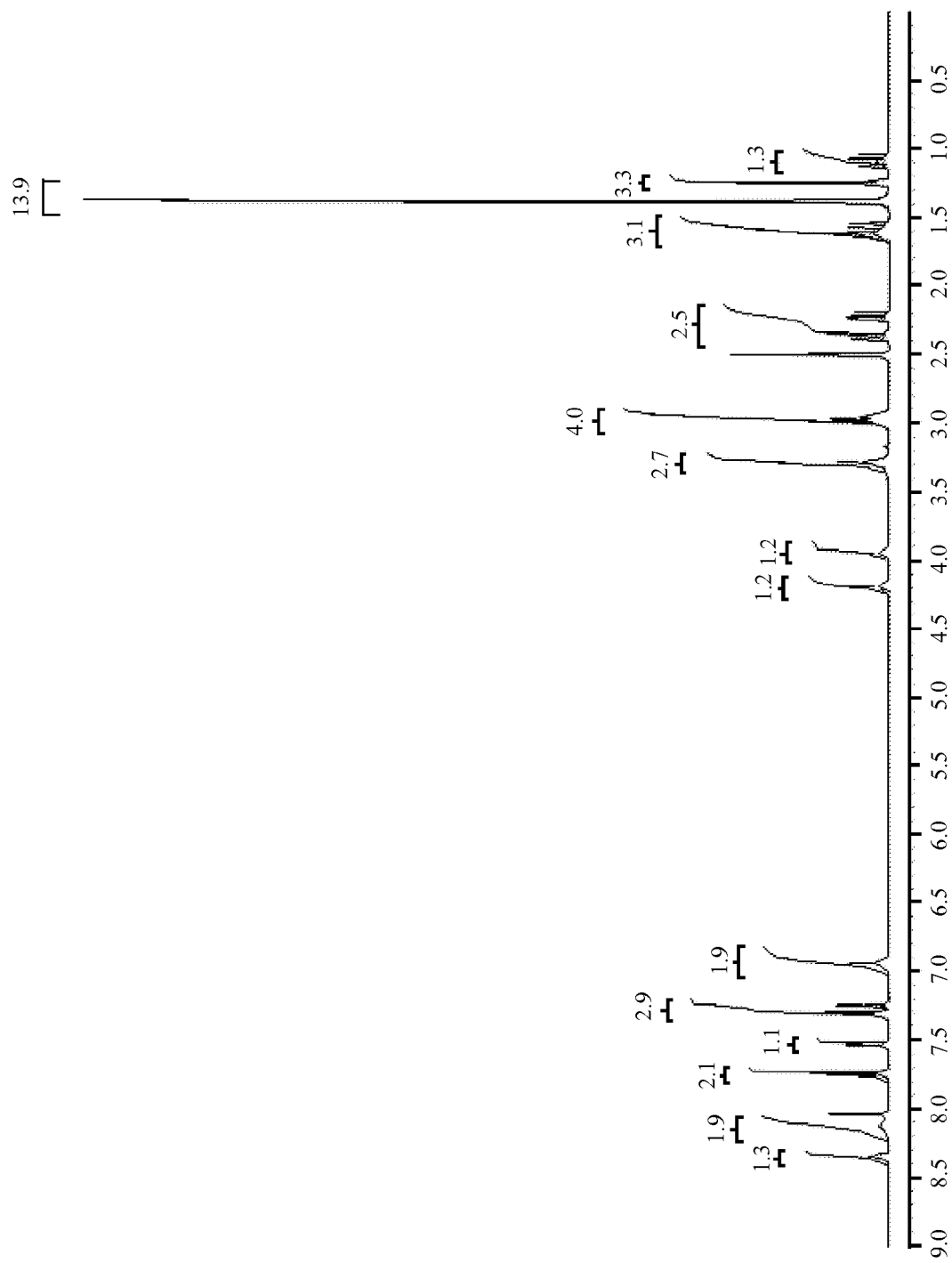
Figure 2:
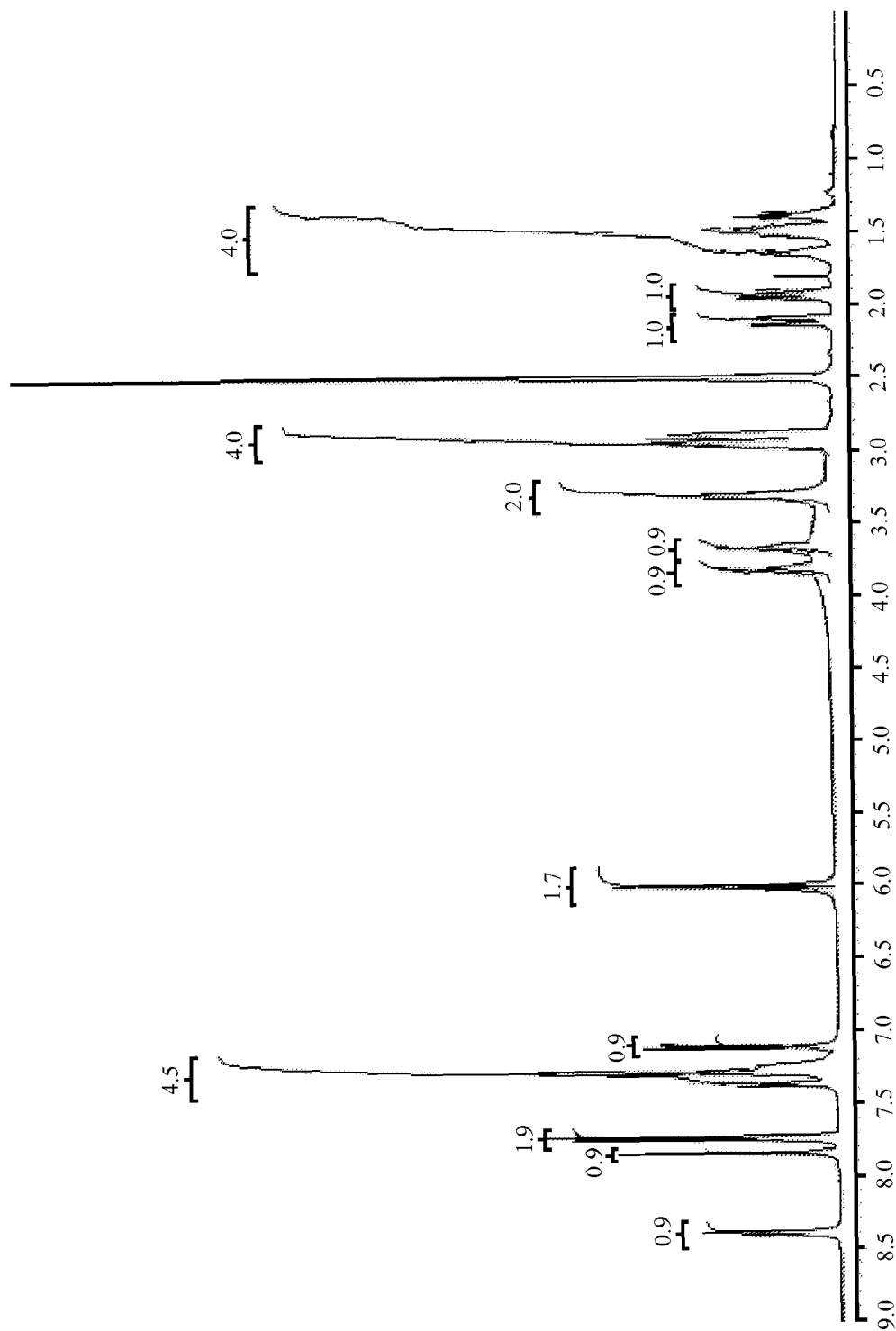
Figure 3:
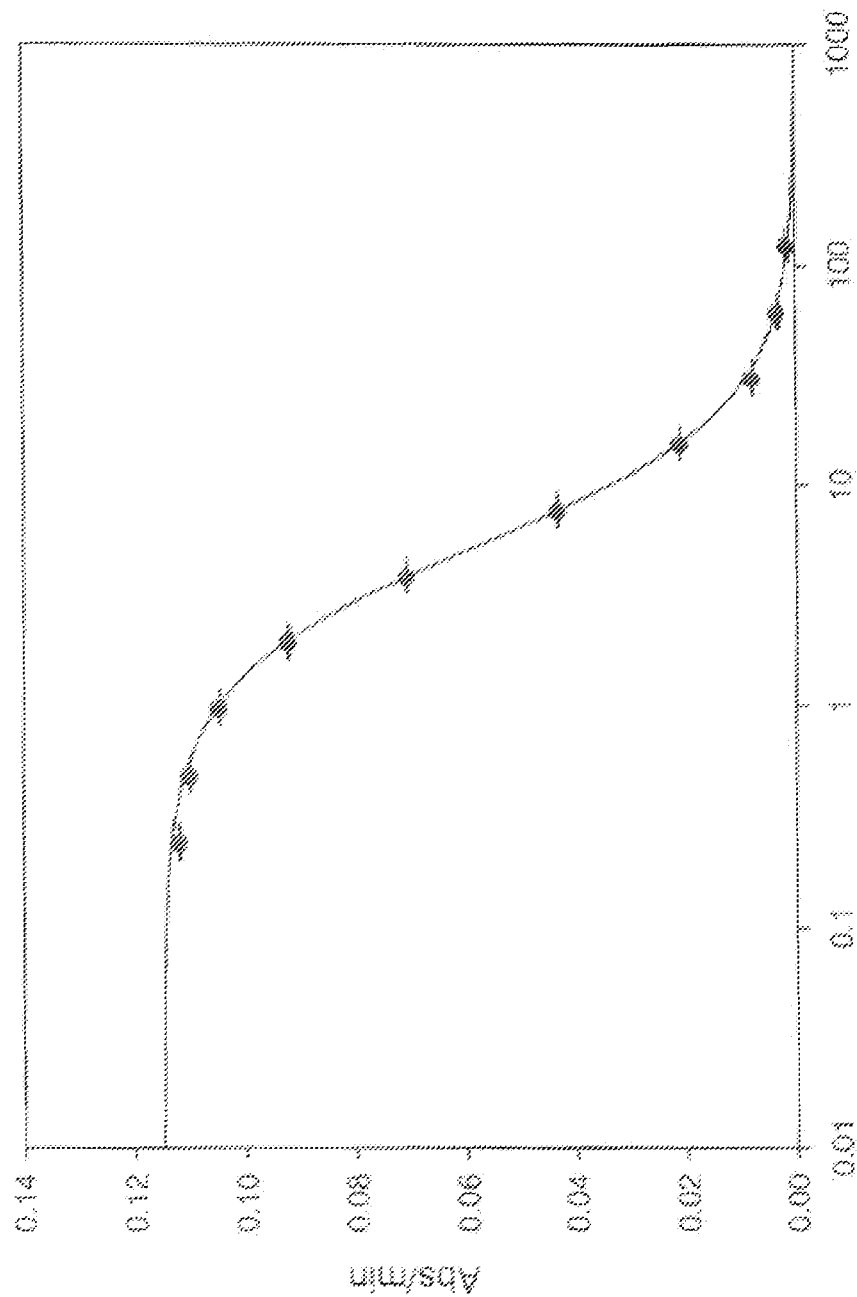
Figure 4:
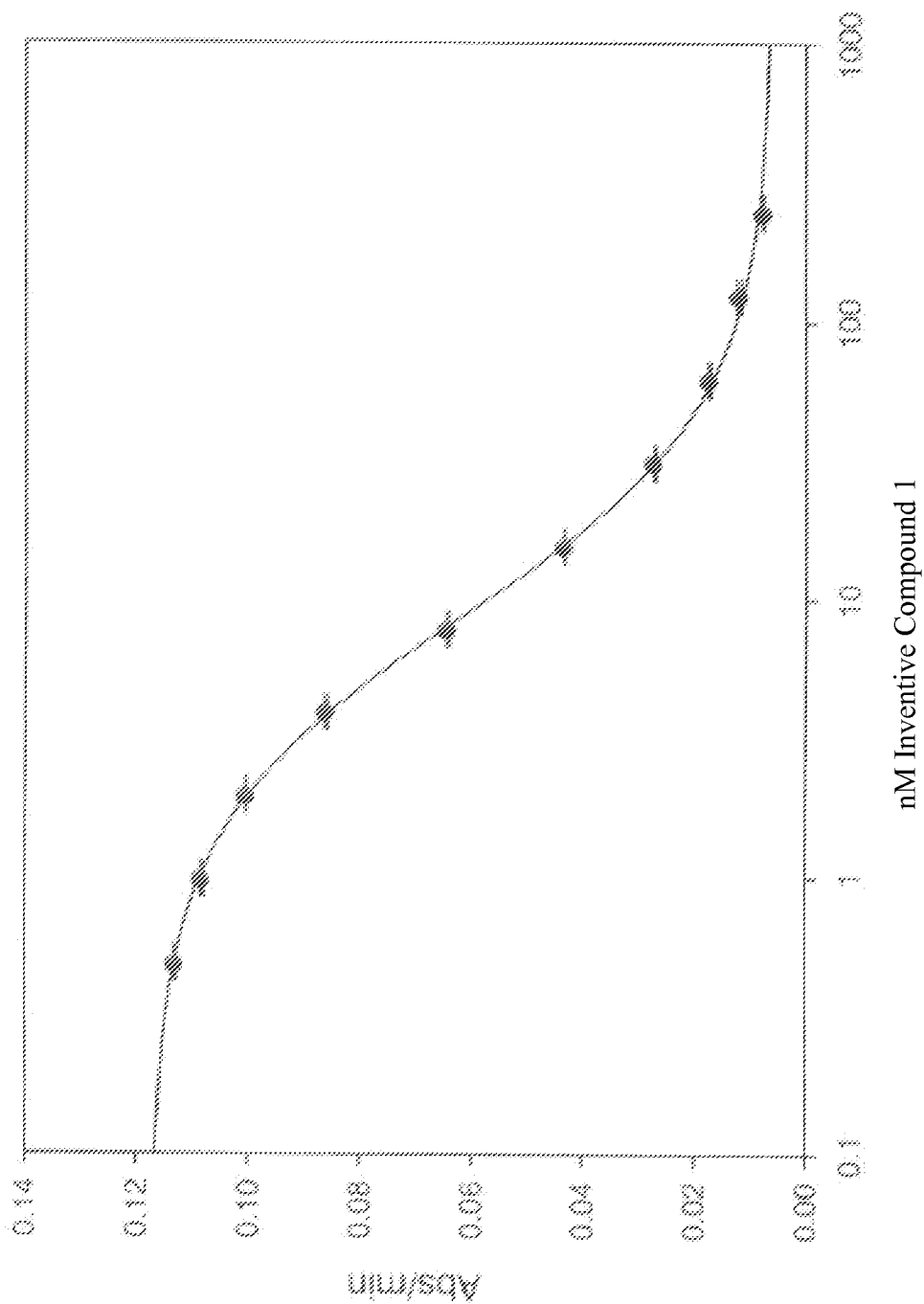
Figure 5:
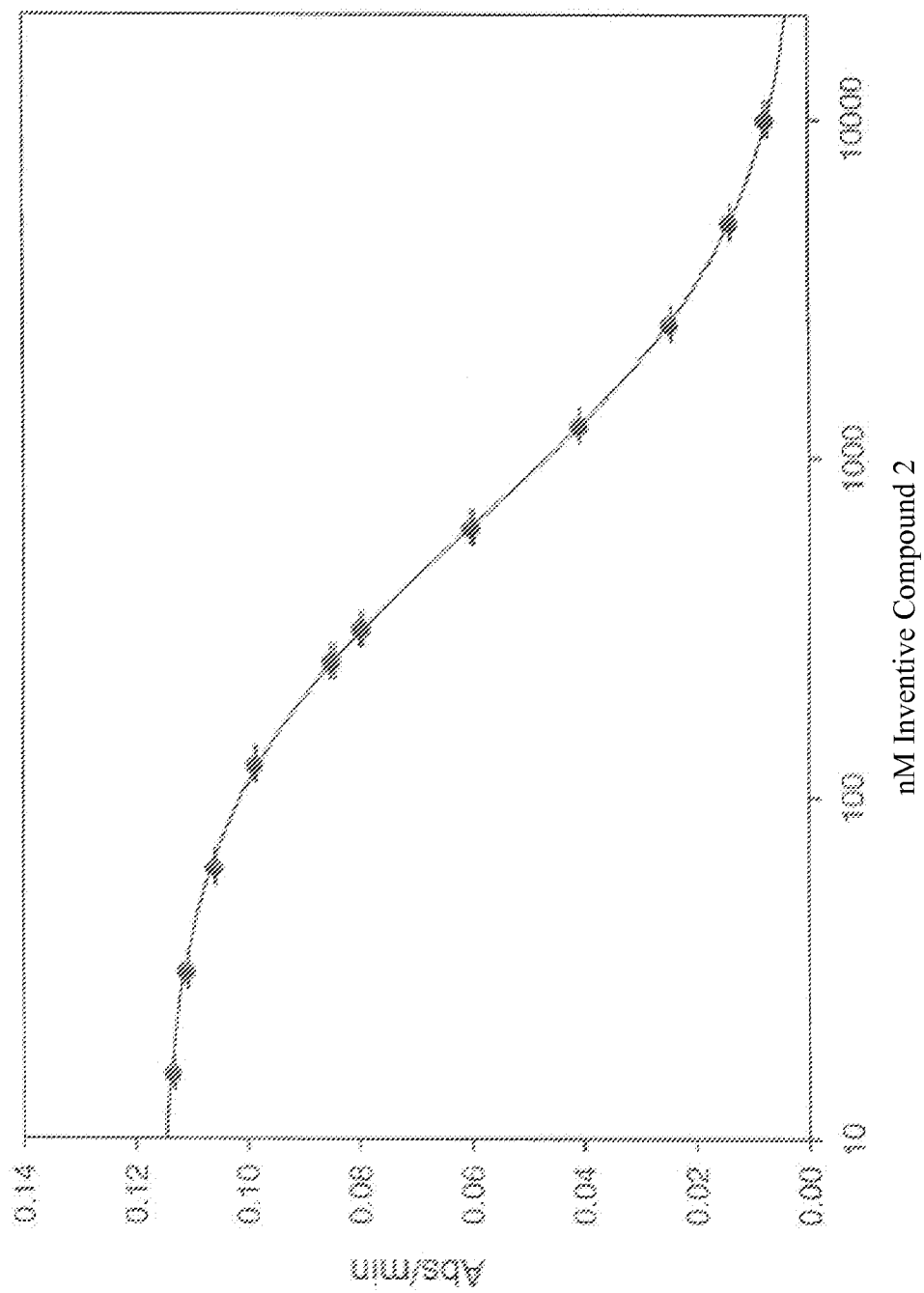
Figure 6:
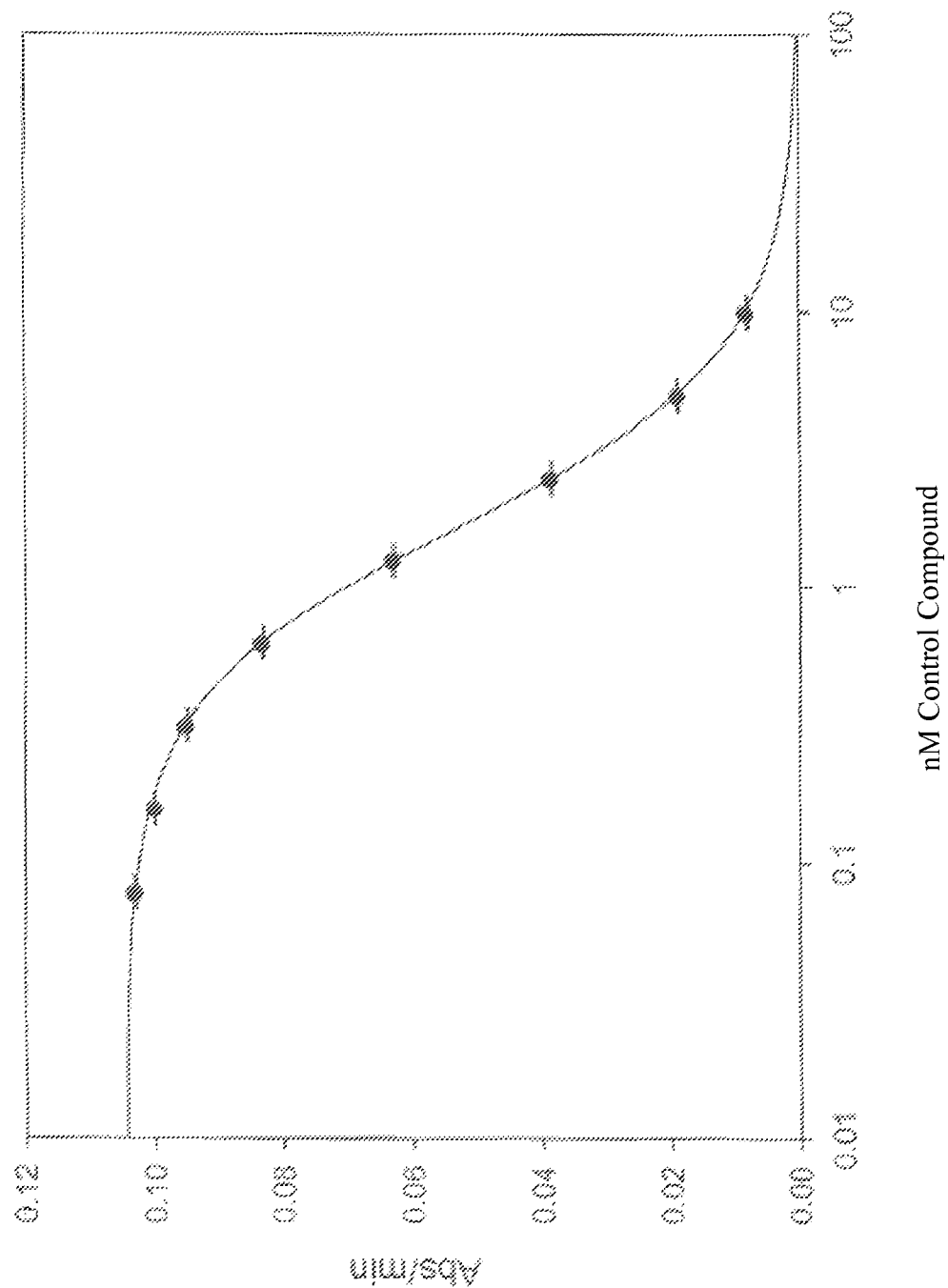

Having thus described the invention in general terms, reference will now be made to the accompanying drawings, which are not necessarily drawn to scale, and wherein:

FIG. 1 is an NMR spectrum of an enzyme inhibiting compound prepared according to one embodiment of the invention;

FIG. 2 is an NMR spectrum of an enzyme inhibiting compound prepared according to another embodiment of the invention;

FIG. 3 is a dose response curve showing average enzyme activity versus the test concentration used to calculate IC50 for the Comparative compound—the compound of Formula (6)—in a human DHFR assay;

FIG. 4 is a dose response curve showing average enzyme activity versus the test concentration used to calculate IC50 for Inventive compound 1—the compound of Formula (23)—in a human DHFR assay;

FIG. 5 is a dose response curve showing average enzyme activity versus the test concentration used to calculate IC50 for Inventive compound 2—the compound of Formula (24)—in a human DHFR assay; and FIG. 6 is a dose response curve showing average enzyme activity versus the test concentration used to calculate IC50 for the Control compound—methotrexate—in a human DHFR assay.

DETAILED DESCRIPTION OF THE INVENTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

I. Definitions

The terms "metabolically inert antifolate" or "antifolate" as used herein mean compounds that are folic acid analogs capable of disrupting folate metabolism and are, optionally, non-polyglutamylatable. In certain embodiments, the term can mean compounds that are also non-hydroxylatable.

The term "alkali metal" as used herein means Group IA elements and particularly includes sodium, lithium, and potassium; the term "alkali metal salt" as used herein means an ionic compound wherein the cation moiety of the compound comprises an alkali metal, particularly sodium, lithium, or potassium.

The term "alkyl" as used herein means saturated straight, branched, or cyclic hydrocarbon groups. In particular embodiments, alkyl refers to groups comprising 1 to 10 carbon atoms ("$C_{1-10}$ alkyl"). In further embodiments, alkyl refers to groups comprising 1 to 8 carbon atoms ("$C_{1-8}$ alkyl"), 1 to 6 carbon atoms ("$C_{1-6}$ alkyl"), or 1 to 4 carbon atoms ("$C_{1-4}$ alkyl"). In specific embodiments, alkyl refers to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethybutyl, and 2,3-dimethylbutyl. Substituted alkyl refers to alkyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$), or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

The term "alkenyl" as used herein means alkyl moieties wherein at least one saturated C—C bond is replaced by a double bond. In particular embodiments, alkenyl refers to groups comprising 2 to 10 carbon atoms ("$C_{2-10}$ alkenyl"). In further embodiments, alkyl refers to groups comprising 2 to 8 carbon atoms ("$C_{2-8}$ alkenyl"), 2 to 6 carbon atoms ("$C_{2-6}$ alkenyl"), or 2 to 4 carbon atoms ("$C_{2-4}$ alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "alkynyl" as used herein means alkyl moieties wherein at least one saturated C—C bond is replaced by a triple bond. In particular embodiments, alkynyl refers to groups comprising 2 to 10 carbon atoms ("$C_{2-10}$ alkynyl"). In further embodiments, alkyl refers to groups comprising 2 to 8 carbon atoms ("$C_{2-8}$ alkynyl"), 2 to 6 carbon atoms ("$C_{2-6}$ alkynyl"), or 2 to 4 carbon atoms ("$C_{2-4}$ alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1- hexynyl, 2-hexynyl, 3-hexynyl, 4-hexynyl, or 5-hexynyl.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("$C_{1-10}$ alkoxy"). In further embodiments, alkoxy refers to oxygen-linked groups comprising 1 to 8 carbon atoms ("$C_{1-8}$ alkoxy"), 1 to 6 carbon atoms ("$C_{1-6}$ alkoxy"), or 1 to 4 carbon atoms ("$C_{1-4}$ alkoxy").

The term "halo" or "halogen" as used herein means fluorine, chlorine, bromine, or iodine.

The term "aryl" as used herein means a stable monocyclic, bicyclic, or tricyclic carbon ring of up to 8 members in each ring, wherein at least one ring is aromatic as defined by the Hückel 4n+2 rule. Exemplary aryl groups according to the invention include phenyl, naphthyl, tetrahydronaphthyl, and biphenyl.

The terms "aralkyl" and "arylalkyl" as used herein mean an aryl group as defined above linked to the molecule through an alkyl group as defined above.

The terms "alkaryl" and "alkylaryl" as used herein means an alkyl group as defined above linked to the molecule through an aryl group as defined above.

The term "acyl" as used herein means a carboxylic acid ester in which the non-carbonyl moiety of the ester group is selected from straight, branched, or cyclic alkyl or lower alkyl; alkoxyalkyl including methoxymethyl; aralkyl including benzyl; aryloxyalkyl such as phenoxymethyl; aryl including phenyl optionally substituted with halogen, $C_1$-$C_6$ alkyl or $C_1$-$C_6$ alkoxy; sulfonate esters such as alkyl or aralkyl sulphonyl including methanesulfonyl; mono-, di-, or triphosphate ester; trityl or monomethoxytrityl; substituted benzyl; trialkylsilyl such as dimethyl-t-butylsilyl or diphenylmethylsilyl. Aryl groups in the esters optimally comprise a phenyl group.

The term "amino" as used herein means a moiety represented by the structure $NR_2$, and includes primary amines, and secondary and tertiary amines substituted by alkyl (i.e., alkylamino). Thus, $R_2$ may represent two hydrogen atoms, two alkyl moieties, or one hydrogen atom and one alkyl moiety.

The terms "alkylamino" and "arylamino" as used herein mean an amino group that has one or two alkyl or aryl substituents, respectively.

The term "nitro" as used herein means a group having the structure $NO_2$;

The term "alkylene" as used herein means an alkyl group having two free valencies (i.e., a divalent alkyl radical);

The term "amide" as used herein means a compound having the general formula $R_1(CO)NR_2R_3$, wherein any of $R_1$, $R_2$, and $R_3$ can be hydrogen or hydrocarbon;

The term "antifolate residue" as used herein means a constituent of a compound exhibiting antifolate activity, the constituent retaining at least a portion of the antifolate activity of the original compound when separated from the original compound.

The term "antifolate segment" as used herein refers to a specific segment of an individual compound that imparts antifolate activity to the overall compound.

The term "analogue" as used herein means a compound in which one or more individual atoms or functional groups have been replaced, either with a different atom or a different functional, generally giving rise to a compound with similar properties.

The term "derivative" as used herein means a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

The term "optionally substituted" in reference to a substituent group refers to substituent groups optionally substituted with one or more moieties, for example, those selected from the group consisting of $C_{1-10}$ alkyl (e.g., $C_{1-6}$ alkyl); $C_{1-10}$ alkoxy (e.g., $C_{1-6}$ alkoxy); $C_{2-10}$ alkenyl; $C_{2-10}$ alkynyl; $C_6$-$C_{12}$ aryl; aryloxy; heteroaryl; heterocycle; halo (e.g., Cl, F, Br, and I); hydroxyl; halogenated alkyl (e.g., $CF_3$, 2-Br-ethyl, $CH_2F$, $CH_2CF_3$, and $CF_2CF_3$); amino (e.g., $NH_2$, $NR_{12}H$, and $NR_{12}R_{13}$); alkylamino; arylamino; acyl; amido; CN; $NO_2$; $N_3$; $CH_2OH$; $CONH_2$; $CONR_{12}R_{13}$; $CO_2R_{12}$; $CH_2OR_{12}$; $NHCOR_{12}$; $NHCO_2R_{12}$; $C_{1-3}$ alkylthio; sulfate; sulfonic acid; sulfonate esters such as alkyl or aralkyl sulfonyl, including methanesulfonyl; phosphonic acid; phosphate; phosphonate; mono-, di-, or triphosphate esters; trityl or monomethoxytrityl; $R_{12}SO$; $R_{12}SO_2$; $CF_3S$; $CF_3SO_2$; and trialkylsilyl, such as dimethyl-t-butylsilyl or diphenylmethylsilyl; wherein $R_{12}$ and $R_{13}$ are each independently selected from H or optionally substituted $C_{1-10}$ alkyl.

The term "analogue" as used herein means a compound in which one or more individual atoms or functional groups have been replaced, either with a different atom or a different functional, generally giving rise to a compound with similar properties.

The term "derivative" as used herein means a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

The term "prodrug" as used herein means any compound which, when administered to a mammal, is converted in whole or in part to a compound of the invention.

The term "active metabolite" as used herein means a physiologically active compound which results from the metabolism of a compound according to the invention, or a prodrug of the compound, when such compound or prodrug is administered to a mammal.

The terms "therapeutically effective amount" or "therapeutically effective dose" as used herein are interchangeable and mean a concentration of a compound according to the invention, or a biologically active variant thereof, sufficient to elicit the desired therapeutic effect according to the methods of treatment described herein.

The term "pharmaceutically acceptable carrier" as used herein means a carrier that is conventionally used in the art to facilitate the storage, administration, and/or the healing effect of a biologically active agent.

The term "intermittent administration" as used herein means administration of a therapeutically effective dose of a composition according to the invention, followed by a time period of discontinuance, which is then followed by another administration of a therapeutically effective dose, and so forth.

The term "antiproliferative agent" as used herein means a compound that decreases the hyperproliferation of cells.

The term "abnormal cell proliferation" as used herein means a disease or condition characterized by the inappropriate growth or multiplication of one or more cell types relative to the growth of that cell type or types in an individual not suffering from that disease or condition.

The term "cancer" as used herein means a disease or condition characterized by uncontrolled, abnormal growth of cells, which can spread locally or through the bloodstream and lymphatic system to other parts of the body. The term includes tumor-forming or non-tumor forming cancers, and includes various types of cancers, such as primary tumors and tumor metastasis.

The term "tumor" as used herein means an abnormal mass of cells within a multicellular organism that results from excessive cell division that is uncontrolled and progressive, also called a neoplasm. A tumor may either be benign or malignant.

The term "fibrotic disorders" as used herein means fibrosis and other medical complications of fibrosis which result in whole or in part from the proliferation of fibroblasts.

The term "arthritis" as used herein means an inflammatory disorder affecting joints that can be infective, autoimmune, or traumatic in origin.

II. Compounds

The present invention is directed to novel compounds exhibiting enzyme inhibiting activities. The invention is made possible by the discovery that the enzyme inhibiting activity of certain antifolate compounds can be retained through the conservation of a specific segment of those compounds. In particular embodiments, the compounds according to the invention comprise a segment imparting enzyme inhibiting activity, preferably antifolate activity.

Molecules exhibiting antifolate activity can be derived from a wide variety of compounds. Methotrexate, the structure of which is provided in Formula (2), is one antifolate that has shown use in cancer treatment, particularly treatment of acute leukemia, non-Hodgkin's lymphoma, breast cancer, head and neck cancer, choriocarcinoma, osteogenic sarcoma, and bladder cancer.

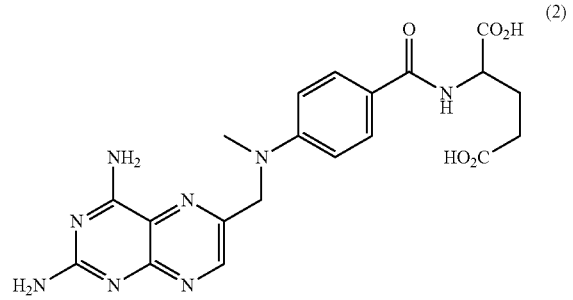 [SMILES: CN(Cc1cnc2nc(N)nc(N)c2n1)c1ccc(C(=O)NC(CCC(=O)O)C(=O)O)cc1]

(2)

Nair et al. (*J. Med. Chem.* (1991) 34:222-227), incorporated herein by reference, demonstrated that polyglutamylation of classical antifolates was not essential for anti-tumor activity and may even be undesirable in that polyglutamylation can lead to a loss of drug pharmacological activity and target specificity. This was followed by the discovery of numerous nonpolyglutamylatable classical antifolates. See Nair et al. (1998) *Proc. Amer. Assoc. Cancer Research* 39:431, which is incorporated herein by reference. One particular group of nonpolyglutamylatable antifolates are characterized by a methylidene group (i.e., a =CH₂ substituent) at the 4-position of the glutamate moiety. The presence of this chemical group has been shown to affect biological activity of the antifolate compound. See Nair et al. (1996) *Cellular Pharmacology* 3:29, which is incorporated herein by reference.

One example of an antifolate having carbon replacement of the secondary amine nitrogen is 4-amino-4-deoxy-10-deazapteroyl-γ-methyleneglutamic acid—more commonly referred to as MDAM—the structure of which is provided in Formula (3).

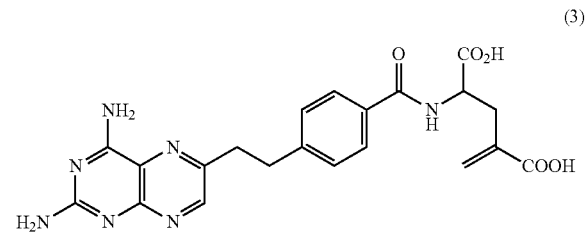 [SMILES: C=C(CC(NC(=O)c1ccc(CCc2cnc3nc(N)nc(N)c3n2)cc1)C(=O)O)C(=O)O]

(3)

The L-enantiomer of MDAM has been shown to exhibit increased physiological activity. See U.S. Pat. No. 5,550,128, which is incorporated herein by reference. Another example of a classical antifolate designed for metabolic stability is ZD1694, which is shown in Formula (4).

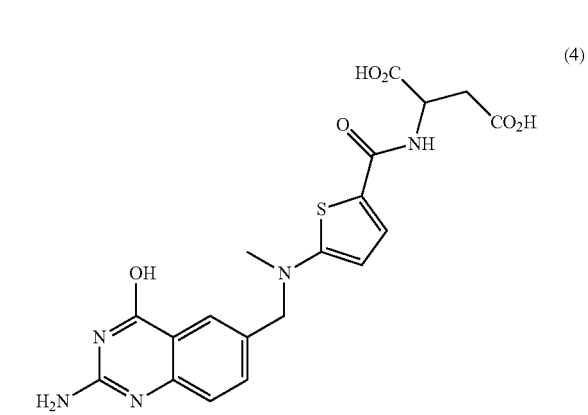 [SMILES: CN(Cc1ccc2nc(N)nc(O)c2c1)c1ccc(C(=O)NC(CC(=O)O)C(=O)O)s1]

(4)

A group of antifolate compounds according to the structure shown in Formula (5) combines several of the molecular features described above.

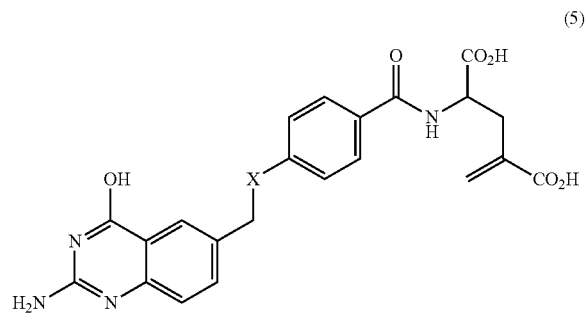

(5)

As shown in Formula (5), X can be $CH_2$, $CHCH_3$, $CH(CH_2CH_3)$, NH, or $NCH_3$. As disclosed in U.S. Pat. No. 5,912,251, which is incorporated herein by reference, the compound M-Trex, wherein X=$CH_2$, has shown activity for the treatment of abnormal cellular proliferation, inflammation disorders, and autoimmune diseases. This compound, which is shown in Formula (6), is known by various names, including the following: 2-{4-[2-(2,4-diamino-quinazolin-6-yl)-ethyl]-benzoylamino}-4-methylidene-pentanedioic acid; gamma methylene glutamate 5,8,10-trideaza aminopterin; and 5,8-dideaza MDAM.

The compound of Formula (6) is non-polyglutamylatable, non-hydroxylatable, and capable of disrupting folate metabolism. The compound has also shown effectiveness in killing large numbers of human leukemia cells and human solid tumor cells in culture at therapeutically relevant concentrations, and has further shown activity as an anti-inflammatory agent in an animal model of asthma.

(6)

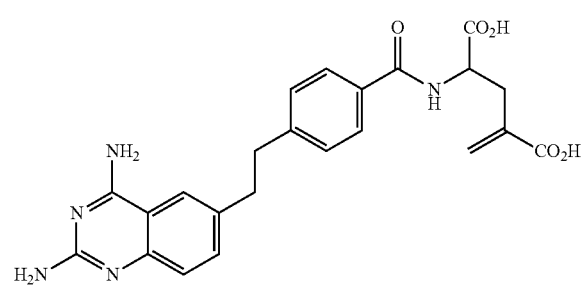

Any of the antifolates described herein may be derivatized to provide an antifolate segment effective in the enzyme inhibitors provided by the present invention. Moreover, non-limiting examples of yet further antifolate compounds that may be derivatized for use according to the present invention include trimetrexate, piritrexim, tomudex, and lomotrexol, which are illustrated in Formula (7) through Formula (10), respectively.

(7)

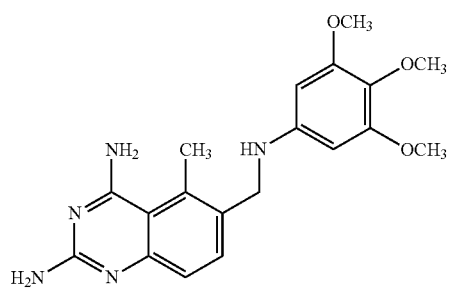

(8)

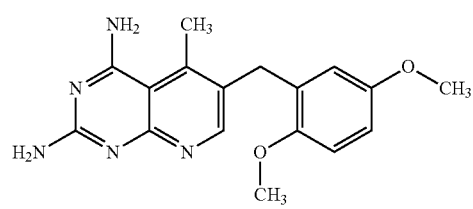

(9)

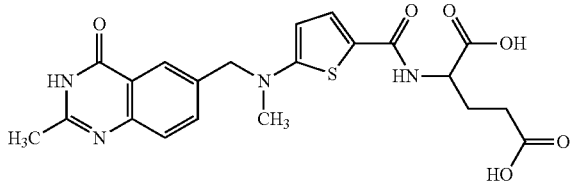

(10)

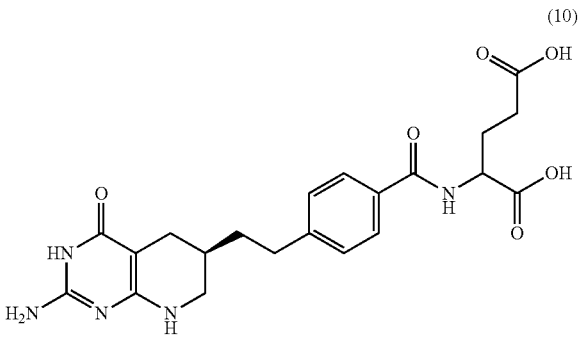

In addition to the foregoing, examples of additional compounds from which molecules exhibiting antifolate activity can be derived are provided in U.S. Patent Application Publication No. 2008/0214585, the disclosure of which is incorporated herein by reference in its entirety. Examples of the antifolate compounds provided therein are shown below in Formula (11)

(11)

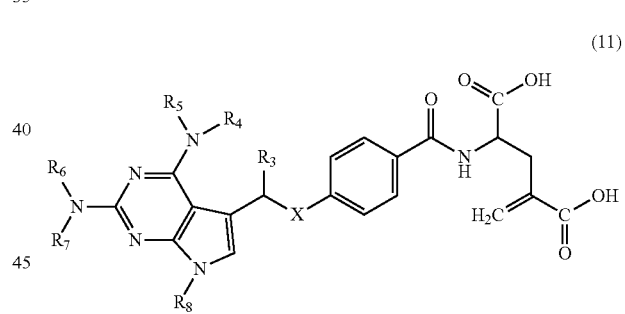

wherein:

X is $CHR_9$ or $NR_9$;

$R_3$ is H, optionally substituted alkyl, optionally substituted alkenyl, optionally substituted alkynyl, optionally substituted alkoxy, hydroxyl, or halo; and $R_4$, $R_5$, $R_6$, $R_7$, $R_8$, and $R_9$ independently are H, optionally substituted alkyl, optionally substituted alkenyl, optionally substituted alkynyl, optionally substituted acyl, —C(O)-alkyl, —C(O)-alkenyl, or —C(O)-alkynyl; and pharmaceutically acceptable esters, amides, salts, solvates, prodrugs, and enantiomers thereof.

One specific example of an additional compound from which molecules exhibiting antifolate activity can be derived is the compound CHL-003, which is shown below in Formula (12).

(12)

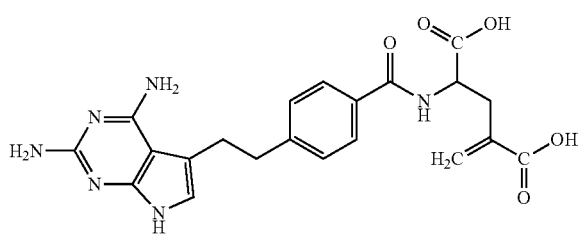

The present invention has realized the ability to conserve the activity of an antifolate compound (including, but not limited to, the antifolate compounds provided above) by derivatizing the compound and retaining at least a residue that imparts at least a portion of the antifolate activity to the antifolate compound. In particular embodiments, the antifolate residue comprises at least a fused ring structure (e.g., a substituted pteridine group or a substituted pyrrolopyrimidine group). With this portion of the antifolate compound conserved, the remaining chemistry of the compound can be altered, such as by adding different substituents.

Of course, a skilled person would understand that a simple pteridine group (which is present in the antifolate compound methotrexate) would not necessarily by itself be expected to function identically to methotrexate since much of the original compound would have been removed. Likewise, a simple pyrrolopyrimidine group (such as present in the antifolate compound CHL-003) would not necessarily by itself be expected to function identically to CHL-003. The present invention, however, has discovered how to utilize a conserved antifolate residue to form new compounds that function as enzyme inhibitor compounds.

In various embodiments, an enzyme inhibiting compound provided according to the present invention can be according to the structure of Formula (13)

(13)

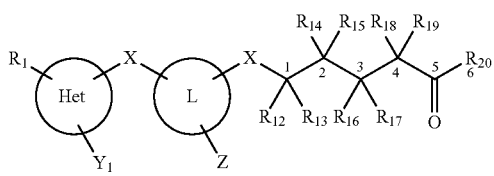

wherein:

Het is an optionally aromatic fused ring structure formed of two fused six-membered rings or a six-membered ring fused with a five-membered ring, one or both of the fused rings comprises up to 3 heteroatoms selected from the group consisting of O, S, and N, and each ring structure may comprise one or more substituents $R_1$ and $Y_1$, as described below, attached to any ring carbon atom or heteroatom (e.g., 0, 1, 2, 3, or 4 total $R_1$ and $Y_1$ groups);

$Y_1$ is selected from the group consisting of H, optionally substituted alkyl, optionally substituted alkenyl, optionally substituted alkynyl, carbonyl, optionally substituted alkoxy, hydroxyl, nitro, halo, optionally substituted acyl, —C(O)-alkyl, —C(O)-alkenyl, —C(O)-alkynyl; and $NR_4R_5$;

$R_1$ is selected from the group consisting of H, optionally substituted alkyl, optionally substituted alkenyl, optionally substituted alkynyl, optionally substituted acyl, —C(O)-alkyl, —C(O)-alkenyl, and —C(O)-alkynyl;

$R_4$ and $R_5$ are independently selected from the group consisting of H, optionally substituted alkyl, optionally substituted alkenyl, optionally substituted alkynyl, optionally substituted acyl, —C(O)-alkyl, —C(O)-alkenyl, and —C(O)-alkynyl;

X is a group selected from amino, amide, oxygen, or alkylene, wherein the alkylene optionally includes one or more heteroatoms (e.g., N or O), and wherein one or more of any carbon or nitrogen atoms of X is optionally substituted with one or more substituents $R_9$;

$R_9$ is selected from the group consisting of H, optionally substituted alkyl, optionally substituted alkenyl, optionally substituted alkynyl, O, optionally substituted acyl, —C(O)-alkyl, —C(O)-alkenyl, —C(O)-alkynyl, optionally substituted alkoxy, hydroxyl, and halo;

L is optional and is selected from an aliphatic group, preferably having 1-12 carbon atoms, or an aromatic or non-aromatic ring structure comprising 5-20 ring atoms, specifically optionally substituted aryl (e.g., $C_5$-$C_{12}$ aryl);

Z is one or more substituents and is selected from the group consisting of H, halo (i.e., chloro, bromo, iodo, or fluoro), optionally substituted alkyl, optionally substituted alkoxy, hydroxyl, carbonyl, $CF_3$, optionally substituted alkenyl, optionally substituted alkynyl, optionally substituted aryl, alkaryl, arylalkyl, optionally substituted heteroaryl, optionally substituted heterocycle, amino, alkylamino, dialkylamino, carboxylic acid, carboxylic ester, carboxamide, nitro, cyano, amide, imide, azide, alkylcarbonyl, optionally substituted acyl, sulfonyl, alkylsulfonyl, sulfinyl, alkylsulfinyl, sulfenyl, alkylsulfenyl, and trialkylammonium;

$R_{12}$, $R_{13}$, $R_{14}$, $R_{15}$, $R_{16}$, $R_{17}$, $R_{18}$, $R_{19}$, and $R_{20}$ are independently selected from the group consisting of H, hydroxyl, optionally substituted alkyl, optionally substituted alkoxy, halo, optionally substituted acyl, and —C(O)-alkyl;

the labeled atoms 1 through 6 may be optionally cyclized forming a six-membered ring, optionally including one or more O ring atoms; and pharmaceutically acceptable esters, amides, salts, solvates, prodrugs, and enantiomers thereof.

In some embodiments, two Z groups may be combined to form a five or six-membered fused ring with L, optionally including one or more heteroatoms in the fused ring, and the fused ring optionally including one or more substituents as described above. It is understood that when a Z group is a substituted group (e.g., substituted alkyl, substituted alkoxy, substituted aryl, substituted heteroaryl, or substituted heterocycle), the substituent on the Z group can in turn be any group included in the definition of Z itself. Likewise, when two or more Z groups form a fused ring that is substituted, any substituent on the fused ring could be any group included in the definition of Z itself.

In certain further embodiments, L is preferably selected from the following ring structures, which may be optionally substituted with one or more Z substituents: phenyl, naphthyl, indyl, azulyl, pentalyl, heptalyl, biphenylenyl, indacenyl, acenaphthyl, phenalyl, imidazolidinyl, indolinyl, isoindolinyl, morpholinyl, piperazinyl, piperidinyl, pyrazolidinyl, pyrrolidinyl, benzofuranyl, carbazolyl, benzopyranyl, furanyl, imidazolyl, indazolyl, indolizinyl, isobenzofuryl, isoindolyl, isoquinolinyl, isothiazolyl, isoxazolyl, naphthyridinyl, oxazolyl, pteridinyl, purinyl, pyranyl, pyrazinyl, pyrazolyl, pyridazinyl, pyridinyl, pyrindinyl, pyrimidinyl, pyrrolyl, pyrrolizinyl, quinazolinyl, quinolinyl, quinolizinyl, quinoxalinyl, thiazolyl, and thiophenyl. Particularly preferred L groups include substituted or unsubstituted pyrrolyl, phenyl, furanyl, pyridinyl, pyrimidinyl, quinolinyl, and naphthyridinyl. In one embodiment, each L group is optionally substituted phenyl, optionally substituted naphthyl, optionally substituted naphthyridinyl, optionally substituted quinolinyl, or an optionally substituted six-membered heteroaryl ring comprising 1-3 nitrogen atoms.

The compounds according to structural Formula (13) have two asymmetric carbon centers—labeled carbon atoms 1 and 3. This symmetry gives rise to four possible isomers: R-cis, S-cis, R-trans, and S-trans. In preferred embodiments, one or both of the asymmetric carbon centers are in trans form. In particularly preferred embodiments, one or both of the asymmetric carbon centers are in the R-trans form.

In other specific embodiments, an enzyme inhibiting compound provided according to the present invention can be according to the structure of Formula (14)

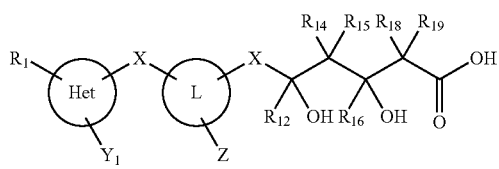
(14)

wherein:

Het, L, $Y_1$, $R_1$, $R_4$, $R_5$, X, $R_9$, Z, $R_{12}$, $R_{14}$, $R_{15}$, $R_{16}$, $R_{18}$, and $R_{19}$ are as described above, and pharmaceutically acceptable esters, amides, salts, solvates, prodrugs, and enantiomers thereof.

In specific embodiments, Het, as described in Formula (13) and Formula (14) above, may be any of the structures provide below in Formula (15) through Formula (18)

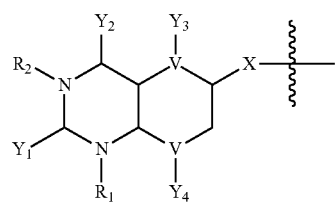
(15)

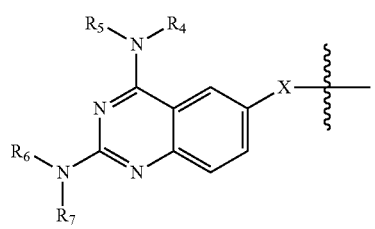
(16)

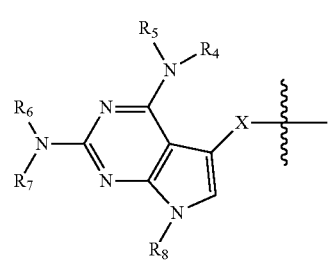
(17)

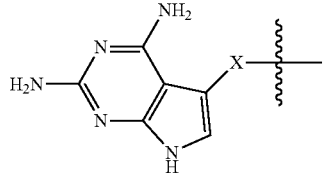
(18)

wherein:

the two six-membered ring fused system is optionally aromatic;

$Y_1$ and $Y_2$ are independently selected from the group consisting of H, optionally substituted alkyl, optionally substituted alkenyl, optionally substituted alkynyl, carbonyl, optionally substituted alkoxy, hydroxyl, nitro, halo, optionally substituted acyl, —C(O)-alkyl, —C(O)-alkenyl, —C(O)-alkynyl; and $NR_4R_5$;

$R_1$, $R_2$, $Y_3$, and $Y_4$ are independently selected from the group consisting of H, optionally substituted alkyl, optionally substituted alkenyl, optionally substituted alkynyl, optionally substituted acyl, —C(O)-alkyl, —C(O)-alkenyl, and —C(O)-alkynyl;

each V is independently C, N, O, or S;

$R_4$, $R_5$, $R_6$, $R_7$, and $R_8$ are independently selected from the group consisting of H, optionally substituted alkyl, optionally substituted alkenyl, optionally substituted alkynyl, optionally substituted acyl, —C(O)-alkyl, —C(O)-alkenyl, and —C(O)-alkynyl;

X is a group selected from amino, amide, oxygen, or alkylene, wherein the alkylene optionally includes one or more heteroatoms (e.g., N or O), and wherein one or more of any carbon or nitrogen atoms of X is optionally substituted with one or more substituents $R_9$;

$R_9$ is selected from the group consisting of H, optionally substituted alkyl, optionally substituted alkenyl, optionally substituted alkynyl, O, optionally substituted acyl, —C(O)-alkyl, —C(O)-alkenyl, —C(O)-alkynyl, optionally substituted alkoxy, hydroxyl, and halo; and the wavy bond indicates the point of attachment to the remaining portion of the structure.

In specific embodiments, an enzyme inhibiting compound provided according to the present invention can be according to the structure of Formula (19) through Formula (22),

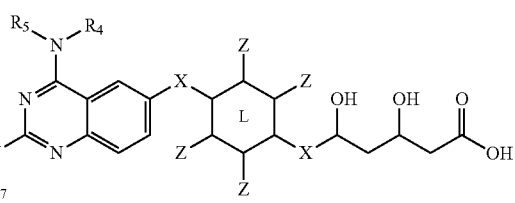
(19)

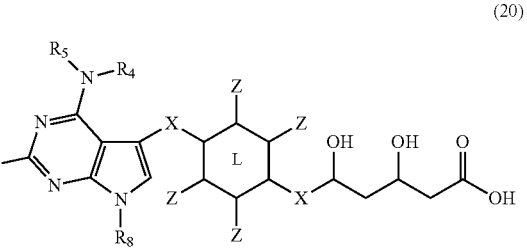
(20)

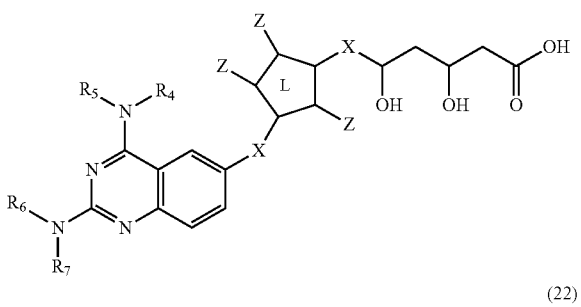

(21)

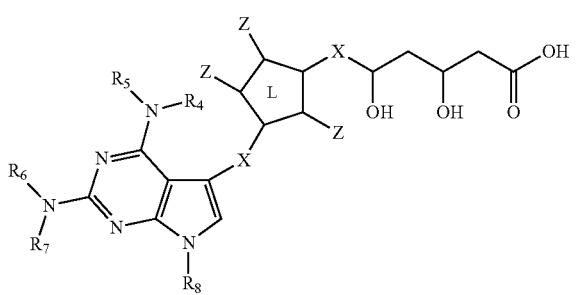

(22)

wherein, in each of Formula (19) through Formula (22):

$R_4$, $R_5$, $R_6$, $R_7$, and $R_8$ are independently selected from the group consisting of H, optionally substituted alkyl, optionally substituted alkenyl, optionally substituted alkynyl, optionally substituted acyl, —C(O)-alkyl, —C(O)-alkenyl, and —C(O)-alkynyl;

X is a group selected from amino, amide, oxygen, or alkylene, wherein the alkylene optionally includes one or more heteroatoms (e.g., N or O), and wherein one or more of any carbon or nitrogen atoms of X is optionally substituted with one or more substituents $R_9$;

$R_9$ is selected from the group consisting of H, optionally substituted alkyl, optionally substituted alkenyl, optionally substituted alkynyl, O, optionally substituted acyl, —C(O)-alkyl, —C(O)-alkenyl, —C(O)-alkynyl, optionally substituted alkoxy, hydroxyl, and halo;

ring structure "L" is optionally aromatic, and one or more ring carbons are optionally replaced with a heteroatom selected from N, O, or S;

each Z is independently selected from the group consisting of H, halo (i.e., chloro, bromo, iodo, or fluoro), optionally substituted alkyl, optionally substituted alkoxy, hydroxyl, carbonyl, $CF_3$, optionally substituted alkenyl, optionally substituted alkynyl, optionally substituted aryl, alkaryl, arylalkyl, optionally substituted heteroaryl, optionally substituted heterocycle, amino, alkylamino, dialkylamino, carboxylic acid, carboxylic ester, carboxamide, nitro, cyano, amide, imide, azide, alkylcarbonyl, optionally substituted acyl, sulfonyl, alkylsulfonyl, sulfinyl, alkylsulfinyl, sulfenyl, alkylsulfenyl, and trialkylammonium; and pharmaceutically acceptable esters, amides, salts, solvates, prodrugs, and enantiomers thereof.

With respect to Formula (19) through Formula (22), examples of X are —$CH_2$—, —$CH_2CH_2$—, —$CH_2CH_2CH_2$—, —$CHR_9$—, —$CH_2CHR_9$—, —$CHR_9CH_2$—, —$CHR_9CH_2CH_2$—, —$CH_2CHR_9CH_2$—, —$NR_9$—, —$CH_2NR_9$—, —$NR_9CH_2$—, —$CH_2CH_2NR_9$—, —$CH_2NR_9CH_2$—, —$NR_9CH_2CH_2$—, —$CHR_9NH$—, —$CHR_9NHCH_2$—, —$NR_9CH_2$—, —C(O)NH—, —C(O)$CH_2NH$—, and —C(O)$NHCH_2$—, preferably $CH_2CH_2$, $CH_2NH$, and C(O)$NHCH_2$; preferred examples of $R_{11}$ are $C_{1-6}$ alkyl and C(O)—$C_{1-6}$ alkyl; preferred examples of $Y_1$ and $Y_2$ are carbonyl, hydroxyl, $C_{1-6}$ alkyl, and $NR_4R_5$; preferred examples of $R_1$, $R_2$, $R_4$, $R_5$, $Y_2$, $Y_3$, and $Y_4$ are H, $C_{1-6}$ alkyl and C(O)$C_{1-6}$ alkyl, wherein each $C_{1-6}$ alkyl can be optionally substituted with one or more halo, halogenated alkyl (e.g., $CF_3$, 2-Br-ethyl, $CH_2F$, $CH_2Cl$, $CH_2CF_3$, or $CF_2CF_3$), hydroxyl, amino, carboxylate, carboxamide, alkylamino, arylamino, alkoxy, aryloxy, nitro, azido, cyano, thio, sulfonic acid, sulfate, phosphonic acid, phosphate, and phosphonate; preferred examples of Z include H, $C_{1-6}$ alkyl, $C_{1-6}$ alkyoxy, phenyl, halo substituted phenyl, and carboxyaniline; preferred examples of alkylene include $C_1$-$C_{10}$, $C_1$-$C_8$, $C_1$-$C_6$, $C_1$-$C_4$, and $C_1$-$C_3$; and preferred examples of $R_{12}$, $R_{13}$, $R_{14}$, $R_{15}$, and $R_{16}$ include H, hydroxyl, $C_{1-6}$ alkyl.

In one particular embodiment, the present invention provides a novel enzyme inhibiting compound having the structure provided in Formula (23), which may be referred to herein as CHL-015.

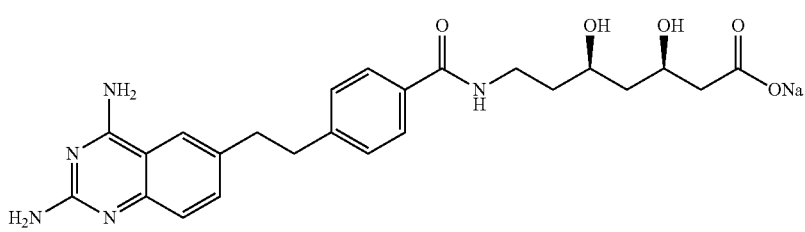

(23)

In another particular embodiment, the present invention provides a novel enzyme inhibiting compound having the structure provided in Formula (24), which may be referred to herein as CHL-016.

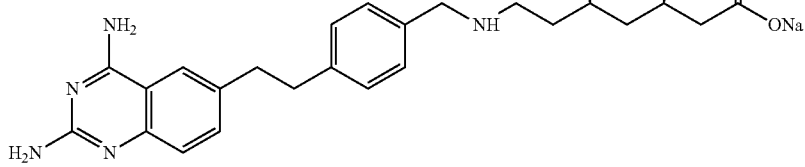

(24)

Although the compounds of Formula (23) and Formula (24) are shown as sodium salts, the present invention also encompasses other pharmaceutically acceptable salts forms (e.g., potassium salts), as well as the acid forms of the compounds.

Various processes can be used for preparing the compounds of the invention exhibiting enzyme inhibiting activity. A specific example of a synthetic process for preparing the compound of Formula (23) is provided in the Experimental section appended hereto.

For example, in certain embodiments, a method of preparing an enzyme inhibiting compound according to the invention can comprise the following steps:
  i) Providing an antifolate residue with a reactive group (e.g., an acid group);
  ii) Providing a reactant having a complementary reactive group to that of the antifolate residue, preferably a protected group (i.e., having reactive oxygen groups thereon being protected from intermediate reaction);
  iii) Reacting the antifolate residue with the reactant, optionally in the presence of a coupling agent; and
  iv) Deprotecting the protected group.

In a specific example, the antifolate residue could comprise a benzoic acid group, the acid functionality being the reactive leaving group, and the remaining phenyl ring comprising at least a portion of the linking group. Of course, further reaction steps could be provided.

III. Biologically Active Variants

Biologically active variants of the enzyme inhibiting compounds set forth above are particularly also encompassed by the invention. Such variants should retain the general biological activity of the original compounds; however, the presence of additional activities would not necessarily limit the use thereof in the present invention. Such activity may be evaluated using standard testing methods and bioassays recognizable by the skilled artisan in the field as generally being useful for identifying such activity.

According to one embodiment of the invention, suitable biologically active variants comprise one or more analogues or derivatives of the compounds described above. Indeed, compounds such as those described above may give rise to an entire family of analogues or derivatives having similar activity and, therefore, usefulness according to the present invention. Likewise, a single compound, such as those described above, may represent a single family member of a greater class of compounds useful according to the present invention. Accordingly, the present invention fully encompasses not only the compounds described above, but analogues and derivatives of such compounds, particularly those identifiable by methods commonly known in the art and recognizable to the skilled artisan.

The compounds disclosed herein may contain chiral centers, which may be either of the (R) or (S) configuration, or may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers. Other isomers are contemplated among the compounds of the present invention. The isomers may be used either in pure form or in admixture with other isomers of the compounds described herein.

Various methods are known in the art for preparing optically active forms and determining activity. Such methods include standard tests described herein other similar tests which are well known in the art. Examples of methods that can be used to obtain optical isomers of the compounds according to the present invention include the following:
  i) physical separation of crystals whereby macroscopic crystals of the individual enantiomers are manually separated. This technique may particularly be used when crystals of the separate enantiomers exist (i.e., the material is a conglomerate), and the crystals are visually distinct;
  ii) simultaneous crystallization whereby the individual enantiomers are separately crystallized from a solution of the racemate, possible only if the latter is a conglomerate in the solid state;
  iii) enzymatic resolutions whereby partial or complete separation of a racemate by virtue of differing rates of reaction for the enantiomers with an enzyme;
  iv) enzymatic asymmetric synthesis, a synthetic technique whereby at least one step of the synthesis uses an enzymatic reaction to obtain an enantiomerically pure or enriched synthetic precursor of the desired enantiomer;
  v) chemical asymmetric synthesis whereby the desired enantiomer is synthesized from an achiral precursor under conditions that produce asymmetry (i.e., chirality) in the product, which may be achieved using chiral catalysts or chiral auxiliaries;
  vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;
  vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;
  viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;
  ix) enantiospecific synthesis from non-racemic precursors whereby the desired enantiomer is obtained from non-chiral starting materials and where the stereochemical integrity is not or is only minimally compromised over the course of the synthesis;
  x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;
  xi) chiral gas chromatography whereby the racemate is volatilized and enantiomers are separated by virtue of their differing interactions in the gaseous mobile phase with a column containing a fixed non-racemic chiral adsorbent phase;
  xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The enzyme inhibiting compounds of the invention may be provided in an enantiomerically enriched form, such as a mixture of enantiomers in which one enantiomer is present in excess (given as a mole fraction or a weight fraction). Enantiomeric excess is understood to exist where a chemical substance comprises two enantiomers of the same compound and one enantiomer is present in a greater amount than the other enantiomer. Unlike racemic mixtures, these mixtures will show a net optical rotation. With knowledge of the specific rotation of the mixture and the specific rotation of the pure enantiomer, the enantiomeric excess (abbreviated "ee") can be determined by known methods. Direct determination of the quantities of each enantiomer present in the mixture is possible with NMR spectroscopy and chiral column chromatography.

In specific embodiments, the compounds of the invention can comprise an enzyme inhibiting compound having an enantiomeric purity for a single enantiomer of at least about 75%. In further embodiments, the enzyme inhibiting compounds of the invention have an enantiomeric purity of at least about 80%, at least about 85%, at least about 90%, at least about 95%, at least about 96%, at least about 97%, at least about 98%, at least about 99%, or at least about 99.5%. In one embodiment, the compounds of the invention comprise an enzyme inhibiting compound having such enantiomeric purity for the (S) isomer. In another embodiment, the compounds of the invention comprise an enzyme inhibiting compound having such enantiomeric purity for the (R) isomer.

The compounds described herein can also be in the form of an ester, amide, salt, solvate, prodrug, or metabolite provided they maintain pharmacological activity according to the present invention. Esters, amides, salts, solvates, prodrugs, and other derivatives of the compounds of the present invention may be prepared according to methods generally known in the art, such as, for example, those methods described by J. March, Advanced Organic Chemistry: Reactions, Mechanisms and Structure, 4$^{th}$ Ed. (New York: Wiley-Interscience, 1992), which is incorporated herein by reference.

Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound useful according to the present invention may be prepared in a similar manner using a pharmaceutically acceptable base, such as sodium hydroxide, potassium hydroxide, ammonium hydroxide, calcium hydroxide, triethylamine, or the like.

Esters of the compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the compositions of the invention may exist in different forms. For example, the compounds may exist in stable and metastable crystalline forms and isotropic and amorphous forms, all of which are intended to be within the scope of the present invention.

If a compound useful according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound of the invention is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

In one particular embodiment, an enzyme inhibiting compound according to the invention is in the form of a salt. For example, the compound of Formula (23) is provided in the form of a sodium salt. Of course, other suitable salt-forming cations could similarly be use. For example, any alkali metal, e.g., sodium, potassium, or calcium, could be used.

The present invention further includes prodrugs and active metabolites of the compounds of the invention. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. In preferred embodiments, the compounds of this invention possess anti-proliferative activity against abnormally proliferating cells, or are metabolized to a compound that exhibits such activity. In other preferred embodiment, the compounds of this invention possess activity for inhibiting activity of the enzyme Dihydrofolate Reductase (DHFR), or are metabolized to a compound that exhibits such activity.

A number of prodrug ligands are known. In general, alkylation, acylation, or other lipophilic modification of one or more heteroatoms of the compound, such as a free amine or carboxylic acid residue, reduces polarity and allows passage into cells. Examples of substituent groups that can replace one or more hydrogen atoms on a free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphotidylcholine; phosphocholine; amino acid residues or derivatives; amino acid acyl residues or derivatives; peptides; cholesterols; or other pharmaceutically acceptable leaving groups which, when administered in vivo, provide the free amine and/or carboxylic acid moiety. Any of these can be used in combination with the disclosed compounds to achieve a desired effect.

IV. Pharmaceutical Compositions

While it is possible for individual compounds according to the present invention to be administered in the raw chemical form, it is preferred for the compounds to be delivered as a pharmaceutical composition. Accordingly, there are provided by the present invention pharmaceutical compositions comprising one or more compounds as described herein. As such, the compositions of the present invention comprise the pharmaceutically active compounds, as described above, or pharmaceutically acceptable esters, amides, salts, solvates, analogs, derivatives, or prodrugs thereof. Further, the inventive compositions can be prepared and delivered in a variety of combinations. For example, the composition can comprise a single composition containing all of the active ingredients. Alternately, the composition can comprise multiple compositions comprising separate active ingredients but intended to be administered simultaneously, in succession, or in otherwise close proximity of time.

The compounds of the invention can be prepared and delivered together with one or more pharmaceutically acceptable carriers therefore, and optionally, other therapeutic ingredients. Carriers should be acceptable in that they are compatible with any other ingredients of the composition and not harmful to the recipient thereof. A carrier may also reduce any undesirable side effects of the agent. Such carriers are known in the art. See, Wang et al. (1980) *J. Parent. Drug Assn.* 34(6):452-462, herein incorporated by reference in its entirety.

Compositions of the present invention may include short-term, rapid-onset, rapid-offset, controlled release, sustained release, delayed release, and pulsatile release compositions, providing the compositions achieve administration of a compound as described herein. See *Remington's Pharmaceutical Sciences* ($18^{th}$ ed.; Mack Publishing Company, Eaton, Pa., 1990), herein incorporated by reference in its entirety. Pharmaceutical compositions according to the present invention are suitable for various modes of delivery, including oral, parenteral (including intravenous, intramuscular, subcutaneous, intradermal, intra-articular, intra-synovial, intrathecal, intra-arterial, intracardiac, subcutaneous, intraorbital, intracapsular, intraspinal, intrastemal, and transdermal), topical (including dermal, buccal, and sublingual), vaginal, urethral, and rectal administration. Administration can also be via nasal spray, surgical implant, internal surgical paint, infusion pump, or via catheter, stent, balloon or other delivery device. The most useful and/or beneficial mode of administration can vary, especially depending upon the condition of the recipient and the disorder being treated.

The pharmaceutical compositions may be conveniently made available in a unit dosage form, whereby such compositions may be prepared by any of the methods generally known in the pharmaceutical arts. Generally speaking, such methods of preparation comprise combining (by various methods) the active compounds of the invention with a suitable carrier or other adjuvant, which may consist of one or more ingredients. The combination of the active ingredients with the one or more adjuvants is then physically treated to present the composition in a suitable form for delivery (e.g., shaping into a tablet or forming an aqueous suspension).

Pharmaceutical compositions according to the present invention suitable for oral dosage may take various forms, such as tablets, capsules, caplets, and wafers (including rapidly dissolving or effervescing), each containing a predetermined amount of the active agent. The compositions may also be in the form of a powder or granules, a solution or suspension in an aqueous or non-aqueous liquid, and as a liquid emulsion (oil-in-water and water-in-oil). The active agents may also be delivered as a bolus, electuary, or paste. It is generally understood that methods of preparations of the above dosage forms are generally known in the art, and any such method would be suitable for the preparation of the respective dosage forms for use in delivery of the compositions according to the present invention.

In one embodiment, compound may be administered orally in combination with a pharmaceutically acceptable vehicle such as an inert diluent or an edible carrier. Oral compositions may be enclosed in hard or soft shell gelatin capsules, may be compressed into tablets or may be incorporated directly with the food of the patient's diet. The percentage of the composition and preparations may be varied; however, the amount of substance in such therapeutically useful compositions is preferably such that an effective dosage level will be obtained.

Hard capsules containing the compound may be made using a physiologically degradable composition, such as gelatin. Such hard capsules comprise the compound, and may further comprise additional ingredients including, for example, an inert solid diluent such as calcium carbonate, calcium phosphate, or kaolin. Soft gelatin capsules containing the compound may be made using a physiologically degradable composition, such as gelatin. Such soft capsules comprise the compound, which may be mixed with water or an oil medium such as peanut oil, liquid paraffin, or olive oil.

Sublingual tablets are designed to dissolve very rapidly. Examples of such compositions include ergotamine tartrate, isosorbide dinitrate, and isoproterenol HCL. The compositions of these tablets contain, in addition to the drug, various soluble excipients, such as lactose, powdered sucrose, dextrose, and mannitol. The solid dosage forms of the present invention may optionally be coated, and examples of suitable coating materials include, but are not limited to, cellulose polymers (such as cellulose acetate phthalate, hydroxypropyl cellulose, hydroxypropyl methylcellulose, hydroxypropyl methylcellulose phthalate, and hydroxypropyl methylcellulose acetate succinate), polyvinyl acetate phthalate, acrylic acid polymers and copolymers, and methacrylic resins (such as those commercially available under the trade name EUDRAGIT®), zein, shellac, and polysaccharides.

Powdered and granular compositions of a pharmaceutical preparation of the invention may be prepared using known methods. Such compositions may be administered directly to a patient or used in the preparation of further dosage forms, such as to form tablets, fill capsules, or prepare an aqueous or oily suspension or solution by addition of an aqueous or oily vehicle thereto. Each of these compositions may further comprise one or more additives, such as dispersing or wetting agents, suspending agents, and preservatives. Additional excipients (e.g., fillers, sweeteners, flavoring, or coloring agents) may also be included in these compositions.

Liquid compositions of the pharmaceutical composition of the invention which are suitable for oral administration may be prepared, packaged, and sold either in liquid form or in the form of a dry product intended for reconstitution with water or another suitable vehicle prior to use.

A tablet containing one or more compounds according to the present invention may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agents.

Adjuvants or accessory ingredients for use in the compositions of the present invention can include any pharmaceutical ingredient commonly deemed acceptable in the art, such as binders, fillers, lubricants, disintegrants, diluents, surfactants, stabilizers, preservatives, flavoring and coloring agents, and the like. Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluloses, algins, gums, and crosslinked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the composition according to the present invention may be anionic, cationic, amphoteric, or nonionic surface active agents. Stabilizers may be included in the compositions to inhibit or lessen reactions leading to decomposition of the active agents, such as oxidative reactions.

Solid dosage forms may be formulated so as to provide a delayed release of the active agents, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agents over a prolonged period of time), and may or may not also be delayed release. Sustained release compositions are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Compositions for parenteral administration include aqueous and non-aqueous sterile injection solutions, which may further contain additional agents, such as anti-oxidants, buffers, bacteriostats, and solutes, which render the compositions isotonic with the blood of the intended recipient. The compositions may include aqueous and non-aqueous sterile suspensions, which contain suspending agents and thickening agents. Such compositions for parenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

The compositions according to the present invention may also be administered transdermally, wherein the active agents are incorporated into a laminated structure (generally referred to as a "patch") that is adapted to remain in intimate contact with the epidermis of the recipient for a prolonged period of time. Typically, such patches are available as single layer "drug-in-adhesive" patches or as multi-layer patches where the active agents are contained in a layer separate from the adhesive layer. Both types of patches also generally contain a backing layer and a liner that is removed prior to attachment to the skin of the recipient. Transdermal drug delivery patches may also be comprised of a reservoir underlying the backing layer that is separated from the skin of the recipient by a semi-permeable membrane and adhesive layer. Transdermal drug delivery may occur through passive diffusion or may be facilitated using electrotransport or iontophoresis.

Compositions for rectal delivery of the compositions of the present invention include rectal suppositories, creams, ointments, and liquids. Suppositories may be presented as the active agents in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

Topical compositions may be in any form suitable and readily known in the art for delivery of active agents to the body surface, including dermally, buccally, and sublingually. Typical examples of topical compositions include ointments, creams, gels, pastes, and solutions. Compositions for topical administration in the mouth also include lozenges.

In certain embodiments, the compounds and compositions disclosed herein can be delivered via a medical device. Such delivery can generally be via any insertable or implantable medical device, including, but not limited to stents, catheters, balloon catheters, shunts, or coils. In one embodiment, the present invention provides medical devices, such as stents, the surface of which is coated with a compound or composition as described herein. The medical device of this invention can be used, for example, in any application for treating, preventing, or otherwise affecting the course of a disease or condition, such as those disclosed herein.

In another embodiment of the invention, the pharmaceutical composition comprising one or more compounds described herein is administered intermittently. Administration of the therapeutically effective dose may be achieved in a continuous manner, as for example with a sustained-release composition, or it may be achieved according to a desired daily dosage regimen, as for example with one, two, three, or more administrations per day. By "time period of discontinuance" is intended a discontinuing of the continuous sustained-released or daily administration of the composition. The time period of discontinuance may be longer or shorter than the period of continuous sustained-release or daily administration. During the time period of discontinuance, the level of the components of the composition in the relevant tissue is substantially below the maximum level obtained during the treatment. The preferred length of the discontinuance period depends on the concentration of the effective dose and the form of composition used. The discontinuance period can be at least 2 days, at least 4 days or at least 1 week. In other embodiments, the period of discontinuance is at least 1 month, 2 months, 3 months, 4 months or greater. When a sustained-release composition is used, the discontinuance period must be extended to account for the greater residence time of the composition in the body. Alternatively, the frequency of administration of the effective dose of the sustained-release composition can be decreased accordingly. An intermittent schedule of administration of a composition of the invention can continue until the desired therapeutic effect, and ultimately treatment of the disease or disorder, is achieved.

Administration of the composition according to the invention comprises administering a single pharmaceutically active compound as described herein;

administering a pharmaceutically active compound as described herein with one or more further pharmaceutically active compounds described herein; or administering one or more pharmaceutically active compounds described herein in combination with one or more further pharmaceutically active compounds (i.e., co-administration). Accordingly, it is recognized that the pharmaceutically active compounds in the compositions of the invention can be administered in a fixed combination (i.e., a single pharmaceutical composition that contains both active materials). Alternatively, the pharmaceutically active compounds may be administered simultaneously (i.e., separate compositions administered at the same time). In another embodiment, the pharmaceutically active compounds are administered sequentially (i.e., administration of one or more pharmaceutically active compounds followed by separate administration or one or more pharmaceutically active compounds). One of skill in the art will recognized that the most preferred method of administration will allow the desired therapeutic effect.

Delivery of a therapeutically effective amount of a composition according to the invention may be obtained via administration of a therapeutically effective dose of the composition. Accordingly, in one embodiment, a therapeutically effective amount is an amount effective to treat abnormal cell proliferation. In another embodiment, a therapeutically effective amount is an amount effective to treat inflammation. In yet another embodiment, a therapeutically effective amount is an amount effective to treat arthritis. In still another embodiment, a therapeutically effective amount is an amount effective to treat asthma.

The active compound is included in the pharmaceutical composition in an amount sufficient to deliver to a patient a therapeutic amount of a compound of the invention in vivo in the absence of serious toxic effects. The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

A therapeutically effective amount according to the invention can be determined based on the body weight of the recipient. For example, in one embodiment, a therapeutically effective amount of one or more compounds of the invention is in the range of about 0.1 µg/kg of body weight to about 5 mg/kg of body weight per day. Alternatively, a therapeutically effective amount can be described in terms of a fixed dose. Therefore, in another embodiment, a therapeutically effective amount of one or more compounds of the invention is in the range of about 0.01 mg to about 500 mg per day. Of course, it is understood that such an amount could be divided into a number of smaller dosages administered throughout the day. The effective dosage range of pharmaceutically acceptable salts and prodrugs can be calculated based on the weight of the parent nucleoside to be delivered. If a salt or prodrug exhibits activity in itself, the effective dosage can be estimated as above using the weight of the salt or prodrug, or by other means known to those skilled in the art.

It is contemplated that the compositions of the invention comprising one or more compounds described herein will be administered in therapeutically effective amounts to a mammal, preferably a human. An effective dose of a compound or composition for treatment of any of the conditions or diseases described herein can be readily determined by the use of conventional techniques and by observing results obtained under analogous circumstances. The effective amount of the compositions would be expected to vary according to the weight, sex, age, and medical history of the subject. Of course, other factors could also influence the effective amount of the composition to be delivered, including, but not limited to, the specific disease involved, the degree of involvement or the severity of the disease, the response of the individual patient, the particular compound administered, the mode of administration, the bioavailability characteristics of the preparation administered, the dose regimen selected, and the use of concomitant medication. The compound is preferentially administered for a sufficient time period to alleviate the undesired symptoms and the clinical signs associated with the condition being treated. Methods to determine efficacy and dosage are known to those skilled in the art. See, for example, Isselbacher et al. (1996) *Harrison's Principles of Internal Medicine* 13 ed., 1814-1882, herein incorporated by reference.

V. Active Agent Combinations

In treating various diseases or conditions according to the invention, the compounds disclosed herein may be administered in various combinations. For example, in one embodiment, a composition according to the invention can comprise a single compound described herein. In another embodiment, a composition according to the invention can comprise two or more compounds according to the invention. In still further embodiments, a composition according to the invention can comprise one or more compounds described herein with one or more further compounds known to have therapeutic properties. For example, the compounds described herein can be administered with one or more toxicity-reducing compounds (e.g., folic acid or leucovorin). In further embodiments, the compounds described herein can be administered with one or more compounds known to be an anti-inflammatory, anti-arthritic, antibiotic, antifungal, antiviral, anti-hypercholesterolemia, anti-hypertensive, or anti-clotting agent. Such further compounds can be provided in combination or alternation with the compounds of the invention. In particular embodiments, the compounds of the invention can be provided in combination with one or more compounds selected from the groups described below.

In the following description, certain compounds useful in combination with the compounds of the present invention may be described in reference to specific diseases or conditions commonly treated using the noted compounds. The disclosure of such diseases or conditions is not intended to limit the scope of the invention and particularly does not limit the diseases or conditions that may be treated using the combinations disclosed herein. Rather such exemplary diseases or conditions are provided only to illustrate the types of diseases and conditions typically treated using the additional compounds.

The compounds of the present invention can, in certain embodiments, be used in combination or alternation with antiproliferative agents. Proliferative disorders are currently treated by a variety of classes of compounds including alkylating agents, antimetabolites, natural products, enzymes, biological response modifiers, miscellaneous agents, radiopharmaceuticals (for example, Y-90 tagged to hormones or antibodies), hormones and antagonists. Any of the antiproliferative agents listed below or any other such therapeutic agents and principles as described in, for example, DeVita, V. T., Jr., Hellmann, S., Rosenberg, S. A.; *Cancer: Principles & Practice of Oncology,* 5th ed., Lippincott-Raven Publishers (1997), can be used in combination with the compounds of the present invention Representative, nonlimiting examples of anti-angiogenesis agents suitable for use in combination with the compounds of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs (I-azetidine-2-carboxylic acid (LACA), cis-hydroxyproline), d,1-3, 4-dehydroproline, thiaproline, alpha,alpha-dipyridyl, beta-aminopropionitrile fumarate, 4-propyl-5-(4-pyridinyl)-2 (3h)-oxazolone, methotrexate, mitoxantrone, heparin, interferons, 2 macroglobulin-serum, chimp-3, chymostatin, beta-cyclodextrin tetradecasulfate, eponemycin, fumagillin, gold sodium thiomalate, d-penicillamine (CDPT), beta-1-anticollagenase-serum, alpha-2-antiplasmin, bisantrene, lobenzarit disodium, n-(2-carboxyphenyl-4-chloroanthronilic acid disodium or "CCA", thalidomide, angostatic steroid, cargboxynaminolmidazole, metalloproteinase inhibitors such as BB94. Other anti-angiogenesis agents include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Representative, nonlimiting examples of alkylating agents suitable for use in combination with the compounds of the present invention include, but are not limited to, Nitrogen Mustards, such as Mechlorethamine (Hodgkin's disease, non-Hodgkin's lymphomas), Cyclophosphamide, Ifosfamide (acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas), Melphalan (L-sarcolysin) (multiple myeloma, breast, ovary), Chlorambucil (chronic lymphocytic leukemia, primary macroglobulinemia, Hodgkin's disease, non-Hodgkin's lymphomas), Ethylenimines and Methylmelamines, such as, Hexamethylmelamine (ovary), Thiotepa (bladder, breast, ovary), Alkyl Sulfonates, such as, Busulfan (chronic granulocytic leukemia), Nitrosoureas, such as, Carmustine (BCNU) (Hodgkin's disease, non-Hodgkin's lymphomas, primary brain tumors, multiple myeloma, malignant melanoma), Lomustine (CCNU) (Hodgkin's disease, non-Hodgkin's lymphomas, primary brain tumors, small-cell lung), Semustine (methyl-CCNU) (primary brain tumors, stomach, colon), Streptozocin (STR) (malignant pancreatic insulinoma, malignant carcinoin, Triazenes, such as, Dacarbazine (DTIC—dimethyltriazenoimidazole-carboxamide) (malignant melanoma, Hodgkin's disease, soft-tissue sarcomas).

Representative, nonlimiting examples of anti-metabolite agents suitable for use in combination with the compounds of the present invention include, but are not limited to, Folic Acid Analogs, such as, Methotrexate (amethopterin) (acute lymphocytic leukemia, choriocarcinoma, mycosis fungoides, breast, head and neck, lung, osteogenic sarcoma), Pyrimidine Analogs, such as Fluorouracil (5-fluorouracil—5-FU) Floxuridine (fluorodeoxyuridine—FUdR) (breast, colon, stomach, pancreas, ovary, head and neck, urinary bladder, premalignant skin lesions) (topical), Cytarabine (cytosine arabinoside) (acute granulocytic and acute lymphocytic leukemias), Purine Analogs and Related Inhibitors, such as, Mercaptopurine (6-mercaptopurine—6-MP) (acute lymphocytic, acute granulocytic and chronic granulocytic leukemia), Thioguanine (6-thioguanine—TG) (acute granulocytic, acute lymphocytic and chronic granulocytic leukemia), Pentostatin (2'-deoxycyoformycin) (hairy cell leukemia, mycosis fungoides, chronic lymphocytic leukemia), Vinca Alkaloids, such as, Vinblastine (VLB) (Hodgkin's disease, non-Hodgkin's lymphomas, breast, testis), Vincristine (acute lymphocytic leukemia, neuroblastoma, Wilms' tumor, rhabdomyosarcoma, Hodgkin's disease, non-Hodgkin's lymphomas, small-cell lung), Epipodophylotoxins, such as Etoposide (testis, small-cell lung and other lung, breast, Hodgkin's disease, non-Hodgkin's lymphomas, acute granulocytic leukemia, Kaposi's sarcoma), Teniposide (testis, small-cell lung and other lung, breast, Hodgkin's disease, non-Hodgkin's lymphomas, acute granulocytic leukemia, Kaposi's sarcoma).

Representative, nonlimiting examples of cytotoxic agents suitable for use in combination with the compounds of the present invention include, but are not limited to: doxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci.

Representative, non-limiting examples of natural products suitable for use in combination with the compounds of the present invention include, but are not limited to: Antibiotics, such as, Dactinomycin (actinonmycin D) (choriocarcinoma, Wilms' tumor rhabdomyosarcoma, testis, Kaposi's sarcoma), Daunorubicin (daunomycin-rubidomycin) (acute granulocytic and acute lymphocytic leukemias), Doxorubicin (soft tissue, osteogenic, and other sarcomas, Hodgkin's disease, non-Hodgkin's lymphomas, acute leukemias, breast, genitourinary thyroid, lung, stomach, neuroblastoma), Bleomycin (testis, head and neck, skin and esophagus lung, and genitourinary tract, Hodgkin's disease, non-Hodgkin's lymphomas), Plicamycin (mithramycin) (testis, malignant hypercalcemia), Mitomycin (mitomycin C) (stomach, cervix, colon, breast, pancreas, bladder, head and neck), Enzymes, such as, L-Asparaginase (acute lymphocytic leukemia), Biological Response Modifiers, such as, Interferon-alpha (hairy cell leukemia, Kaposi's sarcoma, melanoma, carcinoid, renal cell, ovary, bladder, non Hodgkin's lymphomas, mycosis fungoides, multiple myeloma, chronic granulocytic leukemia).

Additional agents that can be used in combination or alternation with the compounds and compositions disclosed herein include, but are not limited to: Platinum Coordination Complexes, such as, Cisplatin (cis-DDP) Carboplatin (testis, ovary, bladder, head and neck, lung, thyroid, cervix, endometrium, neuroblastoma, osteogenic sarcoma); Anthracenedione, such as Mixtozantrone (acute granulocytic leukemia, breast); Substituted Urea, such as, Hydroxyurea (chronic granulocytic leukemia, polycythemia vera, essential thrombocytosis, malignant melanoma); Methylhydrazine Derivatives, such as, Procarbazine (N-methylhydrazine, MIH) (Hodgkin's disease); Adrenocortical Suppressants, such as, Mitotane (o,p'-DDD) (adrenal cortex), Aminoglutethimide (breast); Adrenorticosteriods, such as, Prednisone (acute and chronic lymphocytic leukemias, non-Hodgkin's lymphomas, Hodgkin's disease, breast); Progestins, such as, Hydroxprogesterone caproate, Medroxyprogesterone acetate, Megestrol acetate (endometrium, breast); Steroids, such as, include betamethasone sodium phosphate and betamethasone acetate.

Representative, nonlimiting examples of hormones and antagonists suitable for use in combination with the compounds of the present invention include, but are not limited to, Estrogens: Diethylstibestrol Ethinyl estradiol (breast, prostate); Antiestrogen: Tamoxifen (breast); Androgens: Testosterone propionate Fluxomyesterone (breast); Antiandrogen: Flutamide (prostate); Gonadotropin-Releasing Hormone Analog: Leuprolide (prostate). Other hormones include medroxyprogesterone acetate, estradiol, megestrol acetate, octreotide acetate, diethylstilbestrol diphosphate, testolactone, and goserelin acetate.

The compounds of the present invention can be used in combination or alternation with therapeutic agents used to treat arthritis. Examples of such agents include, but are not limited to, the following:

Nonsteroidal anti-inflammatory drugs (NSAIDs), such as cylcooxygenase-2 (COX-2) inhibitors, aspirin (acetylsalicylic acid), ibuprofen, ketoprofen, and naproxen (e.g., sodium naproxen);

Analgesics, such as acetaminophen, opioid analgesics, and transdermal fentanyl;

Biological response modifiers, such as etanercept, infliximab, adalimumab, anakinra, abatacept, tiruximab, certolizumab pegol, golimumab, ustekinumab, and tocilizumab;

Corticosteroids or steroids, such as glucocorticoids (GC), fluticasone, budesonide, prednisolone, hydrocortisone, adrenaline, Aldosterone, Cortisone Acetate, Desoxymethasone, Dexamethasone, Fluocortolone, Hydrocortisone, Meprednisone, Methylprednisolone, Prednisolone, Prednisone, Prednylidene, Procinonide, Rimexolone, and Suprarenal Cortex;

Disease-modifying antirheumatic drugs (DMARDs), such as hydroxychloroquine, cyclosphosphamide, leflunomide, chlorambucil, the gold compound auranofin, sulfasalazine, minocycline, cyclosporine, toll-like receptor agonists and antagonists, kinase inhibitors (e.g., p38 MAPK), immunosuppressants, and tumor necrosis factor (TNF) blockers (e.g., etanercept, infliximab, and adalimumab);

Fibromyalgia medications, such as amitriptyline, fluoxetine, duloxetine, milnacipran, cylobenzaprine, tramadol, gabapentin, pregabalin, and dual-reuptake inhibitors;

Osteoporosis medications, such as estrogens, parathyroid hormones, bisphosphonates, selective receptor molecules, and bone formation agents;

Gout medications, such as allopurinol, probenecid, losartan, and fenofibrate;

Psoriasis medications, such as acitretin; and

Topical treatments, such as topical NSAIDs and capsaicin.

The compounds of the present invention also can be used in combination or alternation with therapeutic agents used to treat asthma. Examples of such agents include, but are not limited to, the following:

Anti-allergics, such as cromolyn sodium and ketotifen fumarate;

Anti-inflammatories, such as NSAIDs and steroidal anti-inflammatories (e.g., beclomethasone dipropionate, budesonide, dexamethasone sodium phosphate, flunisolide, fluticasone propionate, and triamcinolone acetonide);

Anticholinergics, such as ipratropium bromide, belladonna alkaloids, atropine, and oxitropium bromide;

Antihistamines, such as chlorpheniramine, brompheniramine, diphenhydramine, clemastine, dimenhydrinate, cetirizine, hydroxyzine, meclizine, fexofenadine, loratadine, and enadine;

$\beta_2$-adrenergic agonists (beta agonists), such as albutamol, terbutaline, epinephrine, metaproterenol, ipratropium bromide, ephedra (source of alkaloids), ephedrine, and psuedoephedrine;

Leukotriene Receptor Antagonists, such as zafirlukast and zileuton montelukast;

Xanthines (bronchodilators), such as theophylline, dyphylline, and oxtriphylline; Miscellaneous anti-asthma agents, such as xanthines, methylxanthines, oxitriphylline, aminophylline, phosphodiesterase inhibitors such as zardaverine, calcium antagonists such as nifedipine, and potassium activators such as cromakalim; and Prophylactic agent(s), such as sodium cromoglycate, cromolyn sodium, nedocromil, and ketotifen.

Further, non-limiting examples of active agents that can be used in combination or alternation with the compounds of the present invention include anti-psoriasis agents, anti-Inflammatory Bowel Disease (anti-IBD) agents, anti-chronic obstructive pulmonary disease (anti-COPD) agents, anti-multiple sclerosis agents, and anti-lupus agents. In specific embodiments, the invention particularly can comprise combinations of any of the inventive compounds described herein with methotrexate. Such combinations may be provided in the same formulation. Alternatively, the methotrexate may be combined with the inventive compounds such that the compounds are administered according to different dosing regimens (e.g., once or twice weekly for methotrexate and once, twice, or thrice daily for the inventive compounds).

VI. Articles of Manufacture

The present invention also includes an article of manufacture providing a composition comprising one or more compounds described herein. The article of manufacture may contain one or more of the compounds described herein in combination with one or more further therapeutic agents. The article of manufacture can include a vial or other container that contains a composition suitable for use according to the present invention together with any carrier, either dried or in liquid form. In particular, the article of manufacture can comprise a kit including a container with a composition according to the invention. In such a kit, the composition can be delivered in a variety of combinations. For example, the composition can comprise a single dosage comprising all of the active ingredients. Alternately, where more than one active ingredient is provided, the composition can comprise multiple dosages, each comprising one or more active ingredients, the dosages being intended for administration in combination, in succession, or in other close proximity of time. For example, the dosages could be solid forms (e.g., tablets, caplets, capsules, or the like) or liquid forms (e.g., vials), each comprising a single active ingredient, but being provided in blister packs, bags, or the like, for administration in combination.

The article of manufacture further includes instructions for carrying out the method of the invention. Such instructions may be in various forms, such as a label on the container, an insert included in a box in which the container is packaged, or a variety of computer readable formats. The instructions can also be printed on the box in which the vial is packaged. The instructions contain information such as sufficient dosage and administration information so as to allow the subject or a worker in the field to administer the pharmaceutical composition. It is anticipated that a worker in the field encompasses any doctor, nurse, technician, spouse, or other caregiver that might administer the composition. The pharmaceutical composition can also be self-administered by the subject.

VII. Methods of Treatment

Antifolates can vary as to the folate-dependant metabolic process inhibited thereby, and many antifolates act on a variety of enzymes. In particular, antifolates may act by inhibiting one or more of the enzymes TS, DHFR, FPGS, AICAR Tfase, and GARFT.

Thymidylate synthase (TS) is a rate-limiting enzyme in pyrimidine de novo deoxynucleotide biosynthesis and is therefore often a target for chemotherapeutic strategies. In DNA synthesis, TS plays a central role in reductive methylation of deoxyuridine-5'-monophosphate (dUMP) to deoxythymidine-5'-monophosphate (dTMP). Thus, TS inhibition leads directly to depletion of dTMP and subsequently of 2'-deoxythymidine-5'-triphosphate (dTTP), an essential precursor for DNA. This indirectly results in an accumulation of 2'-deoxyuridine-5'-triphosphate (dUTP) and, therefore, leads to so-called "thymine-less death" due to misincorporation of dUTP into DNA and subsequent excision catalyzed by uracil-DNA glycosylase, which causes DNA damage. Both this DNA damage and the noted imbalance in dTTP/dUTP can induce downstream events, leading to apoptosis (cell death).

Dihydrofolate reductase (DHFR) catalyzes the NADPH-dependent reduction of 7,8-dihydrofolate (DHF or H2F) to 5,6,7,8-tetrahydrofolate (THF or H4F). Thus, DHFR is necessary for maintaining intracellular levels of THF, an essential cofactor in the synthetic pathway of purines, thymidylate, and several amino acids.

Glycinamide ribonucleotide formyltransferase (GAR) and 5-aminoimidazole-4-carboxamide ribonucleotide transformylase (AICAR Tfase) are folate-dependent enzymes in the de novo purine biosynthesis pathway critical to cell division and proliferation. GARFT catalyzes the formation of purines from the reaction of 10-formyltetrahydrofolate (10-FTHF) to THF, and AICAR Tfase catalyzes the formyl transfer from the cofactor 10-FTHF to 5-formyl-AICAR Inhibition of GARFT and AICAR Tfase results in a depletion in intracellular purine levels, which in turn inhibits DNA and RNA synthesis. Ultimately, disruption of DNA and RNA synthesis by GARFT and AICAR Tfase inhibition results in cell death. The antiproliferative effect associated with GARFT and AICAR Tfase inhibition makes them particularly desirable targets for anti-tumor drugs.

Folylpolyglutamyl synthase (FPGS) is an enzyme that has a central role in establishing and maintaining both cytosolic and mitochondrial folylpolyglutamate concentrations and, therefore, is essential for folate homeostasis and the survival of proliferating cells. This enzyme catalyzes the ATP-dependent addition of glutamate moieties to folate and folate derivatives.

Since the enzyme inhibiting compounds of the invention include a conserved antifolate residue, the inventive compounds are useful in any method of treatment that would encompass administration of an antifolate compound. The compounds of the present invention are particularly useful in the treatment of various conditions wherein disruption of folic acid metabolism is beneficial for treating a symptom of the condition or the condition generally.

In certain embodiments, the present invention can comprise methods for treating a condition responsive to inhibition of one or more of dihydrofolate reductase (DHFR), thymidylate synthase (TS), folylpolyglutamyl synthase (FPGS), glycinamide ribonucleotide transformylase (GAR), and aminoimidazole carboxamide ribonucleotide transformylase (AICAR Tfase). In further embodiments, the present invention can comprise methods for treating a condition responsive to antifolate activity.

In particular embodiments, the enzyme inhibiting compounds of the invention are useful in any of the following:

1) A method of inhibiting TS activity;
2) A method of inhibiting DHFR activity;
3) A method of inhibiting GAR activity;
4) A method of inhibiting FPGS activity;
5) A method of inhibiting AICAR Tfase activity;
6) A method of disrupting folic acid metabolism;
7) A method of treating abnormal cell proliferation; or
8) A method of treating cancer.

In addition to the specific activities imparted by the conserved antifolate residue, the enzyme inhibiting compounds of the present invention are also useful in the treatment of a variety of further conditions. For example, the compounds of the invention can be useful in any of the following:

9) A method of treating inflammation;
10) A method of treating inflammatory bowel disease;
11) A method of treating Crohn's disease;
12) A method of treating ulcerative colitis;

13) A method of treating arthritis;
14) A method of treating rheumatoid arthritis;
15) A method of treating osteoarthritis;
16) A method of treating an autoimmune inflammatory disease;
17) A method of treating system lupus erythematosus (SLE);
18) A method of treating psoriasis;
19) A method of treating psoriatic arthritis;
20) A method of treating uveitis;
21) A method of treating asthma;
22) A method of treating cardiovascular disease; or
23) A method of treating atherosclerosis.

Of course, the invention also encompasses combinations of any of the above-recited methods of treatment.

The various methods of the invention can comprise the step of administering to a patient one or more enzyme inhibiting compounds as described herein. In certain embodiments, any of the methods of treatment described herein may comprise administering to a patient any one or a combination of the enzyme inhibiting compounds described according to Formula (13), Formula (14), and Formulas (19)-(24). In specific embodiments, the invention is directed to a method of treating any of the conditions described above by administering to a patient one or a combination of the compounds described according to Formula (23) and Formula (24).

A. Abnormal Cellular Proliferation

Abnormal cell proliferation has been shown to be the root of many diseases and conditions, including cancer and non-cancer disorders which present a serious health threat. Generally, the growth of the abnormal cells, such as in a tumor, exceeds and is uncoordinated with that of normal cells. Furthermore, the abnormal growth of tumor cells generally persists in an abnormal (i.e., excessive) manner after the cessation of stimuli that originally caused the abnormality in the growth of the cells. A benign tumor is characterized by cells that retain their differentiated features and do not divide in a completely uncontrolled manner. A benign tumor is usually localized and nonmetastatic. A malignant tumor (i.e., cancer) is characterized by cells that are undifferentiated, do not respond to the body's growth control signals, and multiply in an uncontrolled manner. Malignant tumors are invasive and capable of metastasis.

Treatment of diseases or conditions of abnormal cellular proliferation comprises methods of killing, inhibiting, or slowing the growth or increase in size of a body or population of abnormally proliferative cells (including tumors or cancerous growths), reducing the number of cells in the population of abnormally proliferative cells, or preventing the spread of abnormally proliferative cells to other anatomic sites, as well as reducing the size of a growth of abnormally proliferative cells. The term "treatment" does not necessarily mean a cure or complete abolition of the disorder of abnormal cell proliferation. Prevention of abnormal cellular proliferation comprises methods which slow, delay, control, or decrease the likelihood of the incidence or onset of such disorders in comparison to that which would occur in the absence of treatment.

Abnormal cellular proliferation, notably hyperproliferation, can occur as a result of a wide variety of factors, including genetic mutation, infection, exposure to toxins, autoimmune disorders, and benign or malignant tumor induction. Hyperproliferative cell disorders include, but are not limited to, skin disorders, blood vessel disorders, cardiovascular disorders, fibrotic disorders, mesangial disorders, autoimmune disorders, graft-versus-host rejection, tumors, and cancers.

Representative, non-limiting types of non-neoplastic abnormal cellular proliferation disorders that can be treated using the present invention include: skin disorders such as psoriasis, eczerma, keratosis, basal cell carcinoma, and squamous cell carcinoma; disorders of the cardiovascular system such as hypertension and vasculo-occlusive diseases (e.g., atherosclerosis, thrombosis and restenosis); blood vessel proliferative disorders such as vasculogenic (formation) and angiogenic (spreading) disorders which result in abnormal proliferation of blood vessels, such as antiogenesis; and disorders associated with the endocrine system such as insulin resistant states including obesity and diabetes mellitus (types 1 & 2).

The invention is useful in the treatment of inflammatory diseases associated with non-neoplastic abnormal cell proliferation. These include, but are not limited to, inflammatory bowel disease (IBD), rheumatoid arthritis (RA), multiple sclerosis (MS), proliferative glomerulonephritis, lupus erythematosus, scleroderma, temporal arteritis, thromboangiitis obliterans, mucocutaneous lymph node syndrome, asthma, host versus graft, thyroiditis, Grave's disease, antigen-induced airway hyperactivity, pulmonary eosinophilia, Guillain-Barre syndrome, allergic rhinitis, myasthenia gravis, human T-lymphotrophic virus type 1-associated myelopathy, herpes simplex encephalitis, inflammatory myopathies, atherosclerosis, and Goodpasture's syndrome.

In a particular embodiment, the compounds of the present invention are useful in the treatment of psoriasis. Psoriasis is an immune-mediated skin disorder characterized by chronic T-cell stimulation by antigen-presenting cells (APC) occurs in the skin. The various types of psoriasis include, for example, plaque psoriasis (i.e., vulgaris psoriasis), pustular psoriasis, guttate psoriasis, inverse psoriasis, erythrodermic psoriasis, psoriatic arthritis, scalp psoriasis and nail psoriasis. Common systemic treatments for psoriasis include methotrexate, cyclosporin and oral retinoids, but their use is limited by toxicity. Up to 40% of patients with psoriasis also develop psoriatic arthritis (Kormeili T et al. Br J Dermatol. (2004) 151(0:3-15).

In further embodiments, the compounds of the present invention are useful in the treatment of blood vessel proliferative disorders, including vasculogenic (formation) and angiogenic (spreading) disorders which result in abnormal proliferation of blood vessels. Other blood vessel proliferative disorders include arthritis and ocular diseases such as diabetic retinopathy. Abnormal neovascularization is also associated with solid tumors. In a particular embodiment, the compounds of the present invention are useful in the treatment of diseases associated with uncontrolled angiogenesis. Representative, non-limiting diseases of abnormal angiogenesis include rheumatoid arthritis, ischemic-reperfusion related brain edema and injury, cortical ischemia, ovarian hyperplasia and hypervascularity, (polycystic ovary syndrome), endometriosis, psoriasis, diabetic retinopathy, and other ocular angiogenic diseases such as retinopathy of prematurity (retrolental fibroplastic), macular degeneration, corneal graft rejection, neuroscular glaucoma, and Oster Webber syndrome. Cancers associated with abnormal blood cell proliferation include hemangioendotheliomas, hemangiomas, and Kaposi's sarcoma.

In further embodiments, the compounds of the present invention are useful in the treatment of disorders of the cardiovascular system involving abnormal cell proliferation.

Such disorders include, for example, hypertension, vasculo-occlusive diseases (e.g., atherosclerosis, thrombosis, and restenosis after angioplasty), acute coronary syndromes (such as unstable angina, myocardial infarction, ischemic and non-ischemic cardiomyopathies, post-MI cardiomyopathy, and myocardial fibrosis), and substance-induced cardiomyopathy.

Vascular injury can also result in endothelial and vascular smooth muscle cell proliferation. The injury can be caused by traumatic events or interventions (e.g., angioplasty, vascular graft, anastomosis, organ transplant) (Clowes A et al. A. J. Vasc. Surg (1991) 13:885). Restenosis (e.g., coronary, carotid, and cerebral lesions) is the main complication of successful balloon angioplasty of the coronary arteries. It is believed to be caused by the release of growth factors as a result of mechanical injury to the endothelial cells lining the coronary arteries.

Other atherosclerotic conditions which can be treated or prevented by means of the present invention include diseases of the arterial walls that involve proliferation of endothelial and/or vascular smooth muscle cells, including complications of diabetes, diabetic glomerulosclerosis, and diabetic retinopathy.

In further embodiments, the compounds of the present invention are useful in the treatment of abnormal cell proliferation disorders associated the endocrine system. Exemplary disorders are insulin resistant states including obesity, diabetes mellitus (types 1 & 2), diabetic retinopathy, macular degeneration associated with diabetes, gestational diabetes, impaired glucose tolerance, polycystic ovarian syndrome, osteoporosis, osteopenia, and accelerated aging of tissues and organs including Werner's syndrome.

In further embodiments, the compounds of the present invention are useful in the treatment of abnormal cell proliferation disorders of the urogenital system. These include, for example, edometriosis, benign prostatic hyperplasia, eiomyoma, polycystic kidney disease, and diabetic nephropathy.

In further embodiments, the compounds of the present invention are useful in the treatment of fibrotic disorders. Medical conditions involving fibrosis include undesirable tissue adhesion resulting from surgery or injury. Non-limiting examples of fibrotic disorders include hepatic cirrhosis and mesangial proliferative cell disorders.

In still further embodiments, abnormal cell proliferation disorders of the tissues and joints can be treated according to the present invention. Such disorders include, for example, Raynaud's phenomenon/disease, Sjogren's Syndrome systemic sclerosis, systemic lupus erythematosus, vasculitides, ankylosing spondylitis, osteoarthritis, reactive arthritis, psoriatic arthritis, and fibromyalgia.

In certain embodiments, abnormal cell proliferation disorders of the pulmonary system can also be treated according to the present invention. These disorders include, for example, asthma, chronic obstructive pulmonary disease (COPD), reactive airway disease, pulmonary fibrosis, and pulmonary hypertension.

Further disorders including an abnormal cellular proliferative component that can be treated according to the invention include Behcet's syndrome, fibrocystic breast disease, fibroadenoma, chronic fatigue syndrome, acute respiratory distress syndrome (ARDS), ischemic heart disease, post-dialysis syndrome, leukemia, acquired immune deficiency syndrome, vasculitis, lipid histiocytosis, septic shock, and familial intestinal polyposes such as Gardner syndrome. Also included in the scope of disorders that may be treated by the compositions and methods of the present invention are virus-induced hyperproliferative diseases including, for example, human papilloma virus-induced disease (e.g., lesions caused by human papilloma virus infection), Epstein-Barr virus-induced disease, scar formation, genital warts, cutaneous warts, and the like.

The compounds of the present invention are further useful in the treatment of conditions and diseases of abnormal cell proliferation including various types of cancers such as primary tumors and tumor metastasis. Specific, non-limiting types of benign tumors that can be treated according to the present invention include hemangiomas, hepatocellular adenoma, cavernous hemangiomas, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, and pyogenic granulomas.

Representative, non-limiting cancers treatable by administering a compound according to the invention include breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, reticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas, malignant melanomas, epidermoid carcinomas, and other carcinomas and sarcomas.

The compounds of the present invention are also useful in preventing or treating proliferative responses associated with organ transplantation which contribute to rejections or other complications. For example, proliferative responses may occur during transplantation of the heart, lung, liver, kidney, and other body organs or organ systems.

B. Inflammation

The compounds of the present invention are also useful in the treatment of diseases characterized by inflammation. Diseases and conditions which have significant inflammatory components are ubiquitous and include, for example, skin disorders, bowel disorders, certain degenerative neurological disorders, arthritis, autoimmune diseases and a variety of other illnesses. Some of these diseases have both an inflammatory and proliferative component, as described above. In particular embodiments the compounds are used to treat inflammatory bowel diseases (IBD), Crohn's disease (CD), ulcerative colitis (UC), chronic obstructive pulmonary disease (COPD), sarcoidosis, or psoriasis. The disclosed compounds are also useful in the treatment of other inflammatory diseases, for example, allergic disorders, skin disorders, transplant rejection, poststreptococcal and autoimmune renal failure, septic shock, systemic inflammatory response syndrome (SIRS), adult respiratory distress syndrome (ARDS), envenomation, systemic lupus erythematosus (SLE), Hashimoto's thyroiditis, autoimmune hemolytic anemias, insulin dependent diabetes mellitus, and rheumatic fever, pelvic inflammatory disease (PID), conjunctivitis, dermatitis, uveitis, and bronchitis.

Inflammatory bowel diseases (IBD) includes several chronic inflammatory conditions, including Crohn's disease (CD) and ulcerative colitis (UC). Both CD and UC are considered "idiopathic" because their etiology is unknown. While Crohn's disease and ulcerative colitis share many symptoms (e.g., diarrhea, abdominal pain, fever, fatigue), ulcerative colitis is limited to the colon whereas Crohn's disease can involve any segment of the gastrointestinal tract. Both diseases may involve extraintestinal manifestations, including arthritis, diseases of the eye (e.g., episcleritis and iritis), skin diseases (e.g., erythema nodosum and pyoderma gangrenosum), urinary complications, gallstones, and anemia. Strokes, retinal thrombi, and pulmonary emboli are not uncommon, because many patients are in a hypercoagulable state.

In one embodiment, the compounds of the invention, including pharmaceutically acceptable salts, prodrugs and esters thereof, are useful in the treatment of inflammatory bowel disease. The inflammatory bowel disease may particularly be Crohn's disease.

Chronic Obstructive Pulmonary Disease, or COPD, is characterized by a not fully reversible airflow limitation which is progressive and associated with an abnormal inflammatory reaction of the lungs. It is one of the most common respiratory conditions of adults, a major cause of chronic morbidity and mortality, and represents a substantial economic and social burden worldwide (Pauwels R A. Lancet. (2004) 364(9434):613-20). Other names for the disorder include, for example, Chronic Obstructive Airways Disease, (COAD); Chronic Obstructive Lung Disease, (COLD), Chronic Airflow Limitation, (CAL or CAFL) and Chronic Airflow Obstruction (COA).

COPD is characterized by chronic inflammation throughout the airways, parenchyma, and pulmonary vasculature. The inflammation involves a multitude of cells, mediators, and inflammatory effects. Mediators include, for example, mediators include proteases, oxidants and toxic peptides. Over time, inflammation damages the lungs and leads to the pathologic changes characteristic of COPD. Manifestations of disease includes both chronic bronchitis and emphysema. Chronic bronchitis is a long-standing inflammation of the airways that produces a lot of mucus, causing wheezing and infections. It is considered chronic if a subject has coughing and mucus on a regular basis for at least three months a year and for two years in a row. Emphysema is a disease that destroys the alveolae and/or bronchae, causing the air sacs to become enlarged, thus making breathing difficult. Most common in COPD patients is the centrilobular form of emphysema. In a particular embodiment, the compounds of the present invention are useful in the treatment of chronic obstructive pulmonary disease.

Sarcoidosis is another chronic inflammatory disease with abnormal cell proliferation. It is a multisystem granulomatous disorder wherein the granulomas are created by angiogenic capillary sprouts constantly providing inflammatory cells.

As noted above, inflammation also plays an important role in the pathogenesis of cardiovascular diseases, including restenosis, atherosclerotic complications resulting from plaque rupture, severe tissue ischemia, and heart failure. Inflammatory changes in the arterial wall, for example, are thought to play a major role in the development of restenosis and atherosclerosis (Ross R. N Engl J Med. (1999) 340: 115-126).

Local inflammation occurs in the formation the plaques also contributes to the weakening of the fibrous cap of the advanced plaque, ultimately resulting in plaque rupture and acute coronary syndromes (Lind L. Atherosclerosis. (2003) 169(2):203-14).

Multiple sclerosis (MS) is a chronic, often debilitating autoimmune disease that affects the central nervous system. MS is characterized by inflammation which results when the body directs antibodies and white blood cells against proteins in the myelin sheath, fatty material which insulates the nerves in the brain and spinal cord. The result may be multiple areas of scarring (sclerosis), which slows or blocks muscle coordination, visual sensation and other nerve signals. In a particular embodiment, the compounds of the present invention are useful in the treatment of multiple sclerosis.

Inflammatory have been shown to be associated with the pathogenesis of neurological disorders, including Parkinson's disease and Alzheimer's disease (Mirza B. et al. Neuroscience (2000) 95(2):425-32; Gupta A. Int J Clin Pract. (2003) 57(1):36-9; Ghatan E. et al. Neurosci Biobehav Rev. (1999) 23(5):615-33).

The invention is also useful in the treatment of, for example, allergic disorders, allergic rhinitis, skin disorders, transplant rejection, poststreptococcal and autoimmune renal failure, septic shock, systemic inflammatory response syndrome (SIRS), adult respiratory distress syndrome (ARDS), envenomation, lupus erythematosus, myasthenia gravis, Grave's disease, Hashimoto's thyroiditis, autoimmune hemolytic anemias, insulin dependent diabetes mellitus, glomerulonephritis, and rheumatic fever, pelvic inflammatory disease (PID), conjunctivitis, dermatitis, bronchitis, and rhinitis.

A high level of C-Reactive Protein (CRP) has been identified as a significant risk factor in contributing to cardiovascular disease. (Int. J. Cardiol. 2008, May 21.) Studies of antifolates (Arthritis Res. Ther. 2006, 8(3), R82, and Arthritis Res. 2002, 4(6), R12) have shown them to be effective at reducing systemic levels of CRP, thereby preventing or treating a major risk factor of cardiovascular disease.

Chronic systemic inflammation may contribute to accelerated atherosclerosis and increased arterial stiffness in patients with rheumatoid arthritis (RA). Slowing down the atherosclerosis progression is very useful considering that in RA and systemic lupus erythematosus (SLE) a premature and rapid progression of atherosclerotic lesions exists.

C. Asthma

The compounds disclosed herein can be used in the treatment of asthma. In recent years, it has become clear that the primary underlying pathology of asthma is airway tissue inflammation (Lemanke (2002) Pediatrics 109(2):368-372; Nagayama et al. (1995) Pediatr Allergy Immunol. 6:204-208). Asthma is associated with a wide range of symptoms and signs, including wheezing, cough, chest tightness, shortness of breath and sputum production. Airway inflammation is a key feature of asthma pathogenesis and its clinical manifestations. Inflammatory cells, including mast cells, eosinophils, and lymphocytes, are present even in the airways of young patients with mild asthma.

Inflammation also plays a role in wheezing disorders, with or without asthma. Asthma is sometimes classified by triggers that may cause an episode (or asthma attack) or things that make asthma worse in certain individuals, such as occupational asthma, exercise induced asthma, nocturnal asthma, or steroid resistant asthma. The compounds of the invention can also be used in the treatment of wheezing disorders, generally.

D. Arthritis and Osteoarthritis

More than 40 million Americans suffer from arthritis, which includes over 100 kinds of rheumatic diseases (i.e., diseases affecting joints, muscle, and connective tissue, which makes up or supports various structures of the body, including tendons, cartilage, blood vessels, and internal organs). Representative types of arthritis include rheumatoid (such as soft-tissue rheumatism and non-articular rheumatism), fibromyalgia, fibrositis, muscular rheumatism, myofascil pain, humeral epicondylitis, frozen shoulder, Tietze's syndrome, fascitis, tendinitis, tenosynovitis, bursitis), juvenile chronic, spondyloarthropaties (ankylosing spondylitis), osteoarthritis, hyperuricemia and arthritis associated with acute gout, chronic gout, and systemic lupus erythematosus.

Hypertrophic arthritis or osteoarthritis is the most common form of arthritis and is characterized by the breakdown of the joint's cartilage. Osteoarthritis is common in people over 65, but may appear earlier. Cartilage breakdown causes bones to rub against each other, pain, and loss of movement. Recently, there has been increasing evidence that inflammation plays an important role in osteoarthritis. Nearly one-third of patients ready to undergo joint replacement surgery for osteoarthritis (OA) had severe inflammation in the synovial fluid that surrounds and protects the joints. The compounds of present invention are thus useful in the treatment of osteoarthritis.

The second most common form of arthritis is rheumatoid arthritis. It is an autoimmune disease that can affect the whole body, causing weakness, fatigue, loss of appetite, and muscle pain. Typically, the age of onset is much earlier than osteoarthritis, between ages 20 and 50. Inflammation begins in the synovial lining and can spread to the entire joint. In another embodiment, the compounds of the present invention are useful in the treatment of rheumatoid arthritis.

EXPERIMENTAL

The present invention will now be described with specific reference to various examples. The following examples are not intended to be limiting of the invention and are rather provided as exemplary embodiments.

Example 1

Preparation of CHL-015—Formula (23)

Preparation of the enzyme inhibiting compound CHL-015 (described herein by Formula (23)) was carried out according to Reaction Scheme I

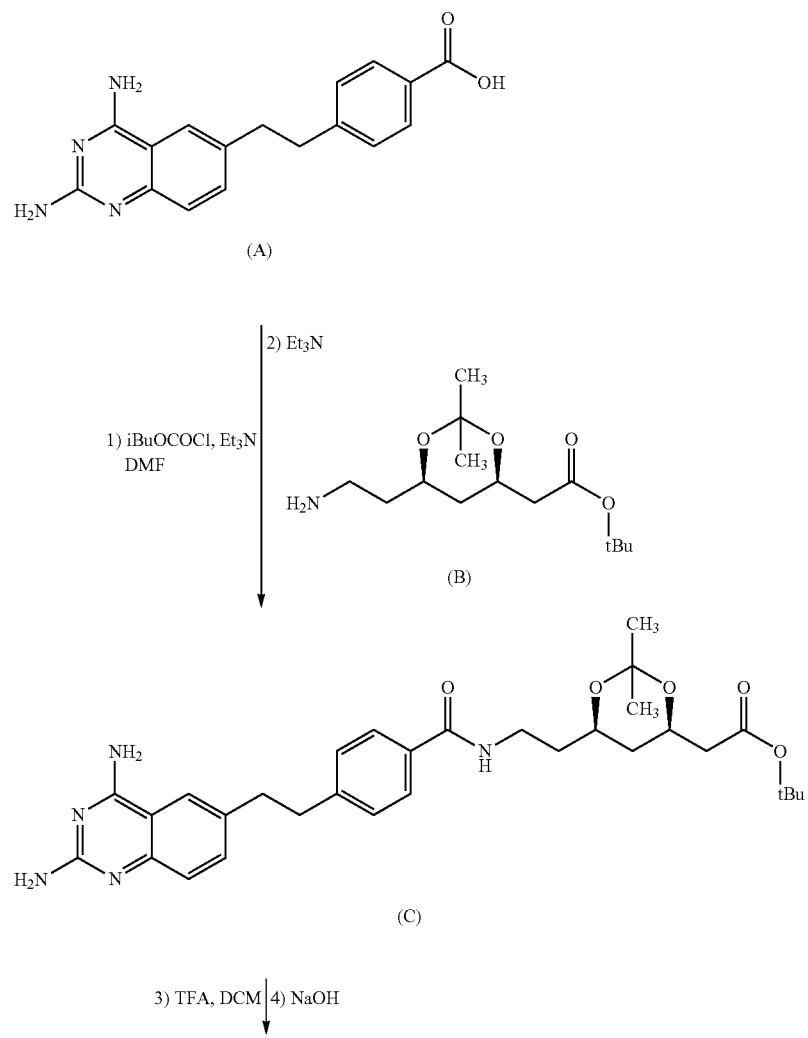

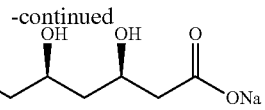
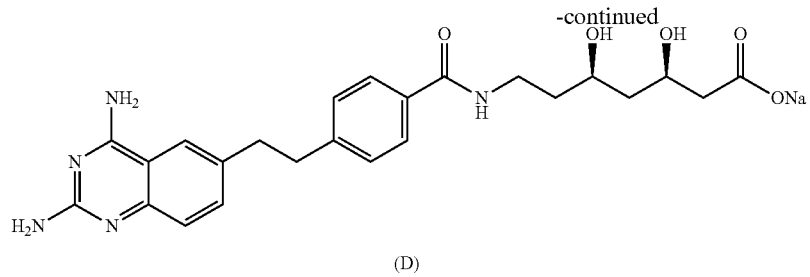

(D)

In the above reaction scheme I, an antifolate residue (compound (A) in reaction scheme I) was used which included a benzoic acid moiety, the acid functional group being used as a leaving group. The antifolate residue was reacted with a coupling agent (isobutyl chloroformate—i.e., iBuOCOCl) in the presence of triethylamine (Et₃N) to form an intermediate anhydride, which was solublized in dimethylformamide (DMF).

The anhydride intermediate solubilized in DMF was reacted with an amine-containing reactant (compound (B) in reaction scheme I) in additional triethylamine. The reaction mixture was filtered, and evaporation of the DMF filtrate left an oil, which was treated with aqueous sodium hydroxide. A solid was formed, which was filtered, washed with water, and dried.

The formed solid intermediate (compound (C) in reaction scheme I) was a completely protected coupling product comprising an intact antifolate residue. This intermediate was purified on silica with a mixture of dichloromethane (DCM) and methanol as the eluent (at a ration of 9:1 to 4:1). This provided 2.68 g. (50% theoretical yield) with 99% purity. The NMR spectra of compound (C) is provided in FIG. 1.

Deprotection of the intermediate compound (C) was carried using a mixture of dichloromethane (DCM) and trofluoroacetic acid (TFA) (1:1). The protecting groups were rapidly removed (i.e., cleavage of the tBu ester and freeing of the two hydroxyl groups), and the mixture was stirred at room temperature until complete conversion (as indicated by liquid chromatography) indicated formation of the lactone. The solvents were removed under reduced pressure, and the residual material was treated with aqueous NaOH to open the lactone ring. To isolate the acid, the basic mixture was acidified with acetic acid, the solid was filtered, and the product was dried. The acid was obtained as a yellow powder at a yield of 1.67 g (77% theoretical yield) and 97% purity (the main impurity being residual lactone).

To prepare the sodium salt (compound (D) in reaction scheme I), the acid was treated with one equivalent of sodium hydroxide as an aqueous solution and the water was evaporated. The yield after drying over phosphorus pentoxide was 1.86 g. The NMR spectrum of compound (D) is provided in FIG. 1. Compound (D) is the compound of Formula (23), as described above.

Example 2

Preparation of CHL-016—Formula (24)

Preparation of the enzyme inhibiting compound CHL-016 (described herein by Formula (24)) was carried out according to the following reaction scheme.

Reaction Scheme II

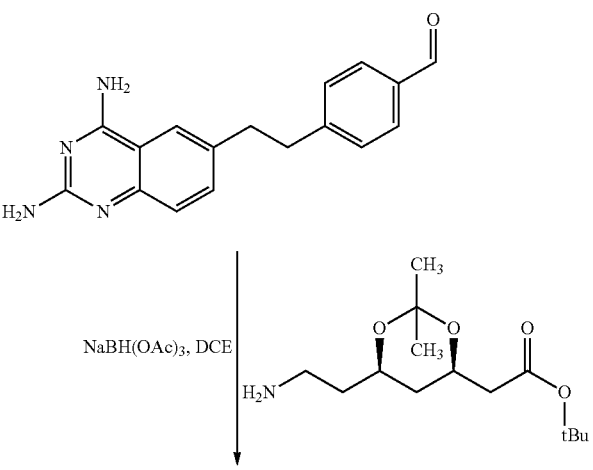

-continued

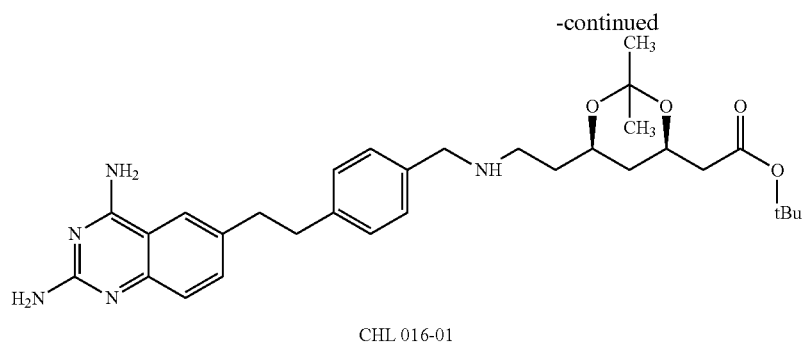

CHL 016-01

1) TFA, DCM  2) NaOH

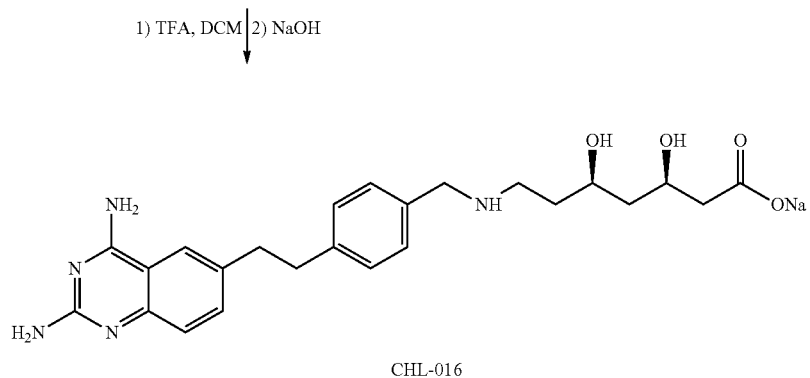

CHL-016

In the above reaction scheme II, an antifolate residue was used which contained a benzaldehyde moiety, the aldehyde functional group being used as a reactive group. The antifolate residue was reacted with the amine-containing reactant by reductive amination in the presence of the acyloxyborohydride, NaBH(OAc)$_3$. The resulting compound (CHL-016-01) was purified on a column chromatography.

Deprotection of the intermediate compound (CHL-016-01) was carried using a mixture of dichloromethane (DCM) and trifluoroacetic acid (TFA) (1:1). The protecting groups were rapidly removed (i.e., cleavage of the tBu ester and freeing of the two hydroxyl groups), and the mixture was stirred at room temperature until complete conversion (as indicated by liquid chromatography) indicated formation of the lactone. The solvents were removed under reduced pressure, and the residual material was treated with aqueous NaOH to open the lactone ring. To isolate the acid, the basic mixture was acidified with a 50% acetic acid solution, the solid was filtered, and the product was dried. The purity of the material was improved by prep-HPLC purification with water/MeCN.

To prepare the sodium salt (compound (CHL-016) in reaction scheme II), the acid was treated with one equivalent of sodium hydroxide as an aqueous solution and the water was evaporated. The yield after drying over phosphorus pentoxide was 0.7 g. The NMR spectrum of CHL-016 is provided in FIG. 2.

Example 3

Inhibition of DHFR

The activity of multiple compounds as inhibitors of human dihydrofolate reductase (DHFR) was evaluated. The dry test compounds were dissolved in 100% DMSO at a concentration of 10 mM. For the test assays, the compounds were serially diluted in 100% DMSO and added to the assays so that the final concentration of DMSO in the assays was 1%. All compounds were fully soluble.

The final assay conditions for the human DHFR assays were: 50 mN KPO$_4$ (pH7.3), 250 mM KCl, 0.1 mM dihydrofolate, 0.1 mM NADPH, 1% DMSO, and 0.2 μg/mL recombinant human DHFR. The final volume of the assay was 800 μL in a semi-micro cuvet.

A decrease in absorbance at 340 nm was monitored for three minutes in a Cary spectrophotometer at 37° C. The concentrations used for each compound across a range of 10,000 to 0.08 nM, depending on the expected level of activity. The assays were done in triplicate for each compound. Methotrexate was tested as a positive control compound. A minimum of seven concentrations were used to generate a curve, and IC$_{50}$ values were calculated using the Standard Curve Analysis of Sigma Plot Enzyme Kinetics software. The test results are shown below in Table 1. Plots for the generated test curves of each compound are shown in FIG. 3 through FIG. 6. In Table 1, the Comparative compound is the compound of Formula (6)—i.e., M-Trex; Inventive compound 1 is the compound of Formula (23); Inventive compound 2 is the compound of Formula (24); and the Control compound is methotrexate (used as a positive control).

TABLE 1

| Compound ID | Human DHFR IC$_{50}$ (nM) | Human DHFR SD of IC$_{50}$ |
|---|---|---|
| Comparative | 5.40 | 0.0821 |
| Inventive 1 | 8.65 | 0.0873 |
| Inventive 2 | 670.3 | 8.0391 |
| Control | 1.86 | 0.0187 |

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An enzyme inhibiting compound according to the structure of any of Formula (19) through Formula (22)

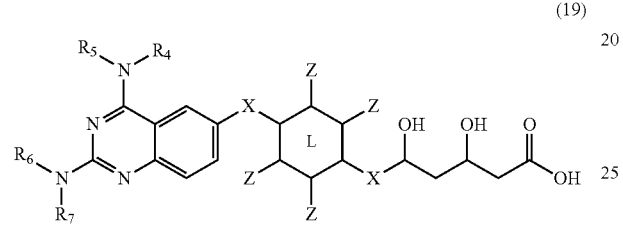

(19)

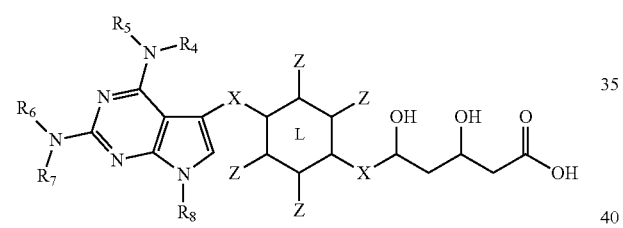

(20)

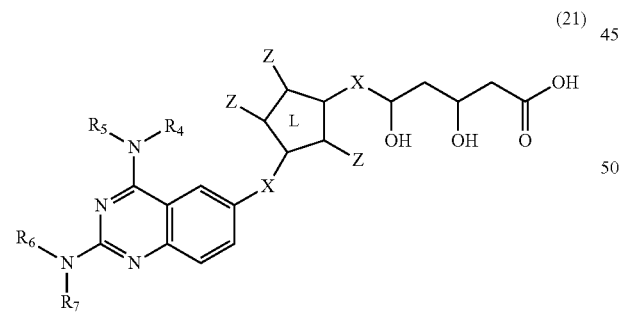

(21)

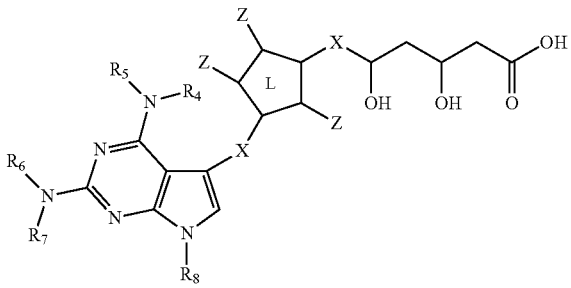

(22)

wherein:

$R_4$, $R_5$, $R_6$, $R_7$, and $R_8$ are independently selected from the group consisting of H, optionally substituted alkyl, optionally substituted alkenyl, optionally substituted alkynyl, optionally substituted acyl, —C(O)-alkyl, —C(O)-alkenyl, and —C(O)-alkynyl;

X is a group selected from amino, amide, oxygen, or alkylene, wherein the alkylene optionally includes one or more heteroatoms, and wherein one or more of any carbon or nitrogen atoms is optionally substituted with one or more substituents $R_9$;

$R_9$ is selected from the group consisting of H, optionally substituted alkyl, optionally substituted alkenyl, optionally substituted alkynyl, O, optionally substituted acyl, —C(O)-alkyl, —C(O)-alkenyl, —C(O)-alkynyl, optionally substituted alkoxy, hydroxyl, and halo;

L is optionally aromatic, and one or more ring carbons are optionally replaced with a heteroatom selected from N, O, or S;

each Z independently is one or more substituents and is selected from the group consisting of H, halo, optionally substituted alkyl, optionally substituted, hydroxyl, carbonyl, $CF_3$, optionally substituted alkenyl, optionally substituted alkynyl, optionally substituted aryl, alkaryl, arylalkyl, optionally substituted heteroaryl, optionally substituted heterocycle, amino, alkylamino, dialkylamino, carboxylic acid, carboxylic ester, carboxamide, nitro, cyano, amide, imide, azide, alkylcarbonyl, optionally substituted acyl, sulfonyl, alkylsulfonyl, sulfinyl, alkylsulfinyl, sulfenyl, alkylsulfenyl, and trialkylammonium; and pharmaceutically acceptable esters, amides, salts, solvates, prodrugs, and enantiomers thereof.

2. An enzyme inhibiting compound according to claim 1, wherein the compound has the structure of Formula (23)

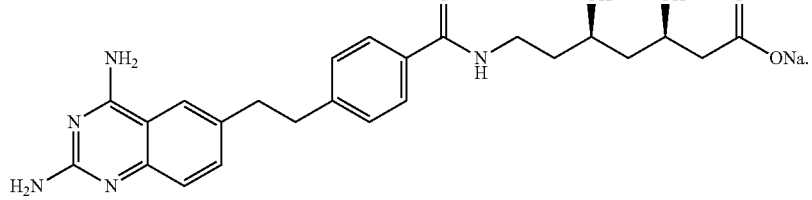

(23)

3. An enzyme inhibiting compound according to claim 1, wherein the compound has the structure of Formula (24)

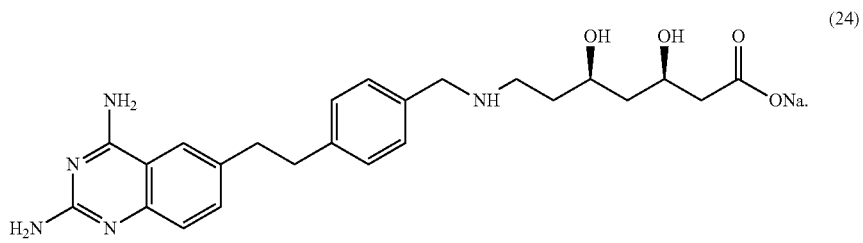

(24)

4. A pharmaceutical composition comprising a pharmaceutically acceptable carrier and an enzyme inhibiting compound according to the structure of any of Formula (19) through Formula (22)

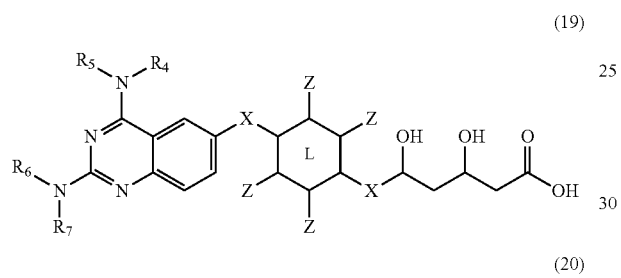

(19)

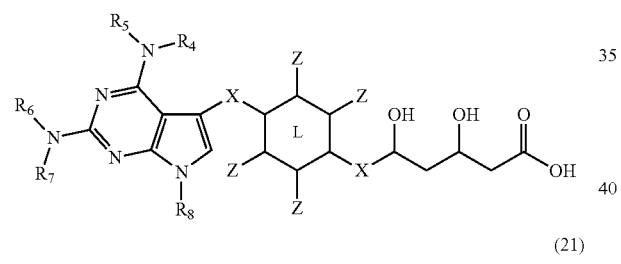

(20)

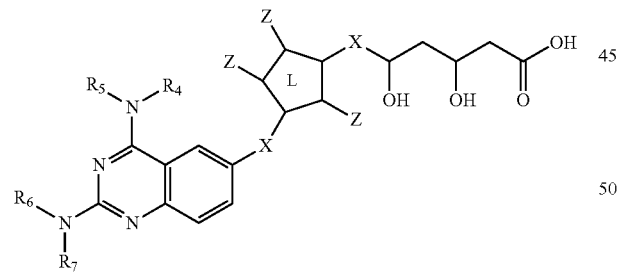

(21)

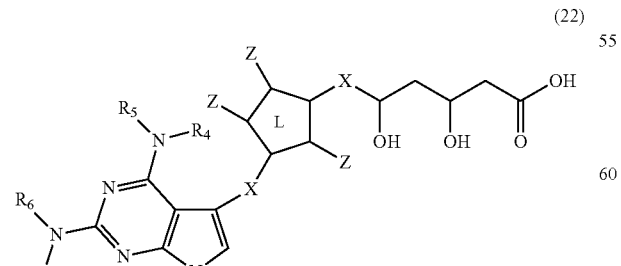

(22)

wherein:

$R_4$, $R_5$, $R_6$, $R_7$, and $R_8$ are independently selected from the group consisting of H, optionally substituted alkyl, optionally substituted alkenyl, optionally substituted alkynyl, optionally substituted acyl, —C(O)-alkyl, —C(O)-alkenyl, and —C(O)-alkynyl;

X is a group selected from amino, amide, oxygen, or alkylene, wherein the alkylene optionally includes one or more heteroatoms, and wherein one or more of any carbon or nitrogen atoms is optionally substituted with one or more substituents $R_9$;

$R_9$ is selected from the group consisting of H, optionally substituted alkyl, optionally substituted alkenyl, optionally substituted alkynyl, O, optionally substituted acyl, —C(O)-alkyl, —C(O)-alkenyl, —C(O)-alkynyl, optionally substituted alkoxy, hydroxyl, and halo;

L is optionally aromatic, and one or more ring carbons are optionally replaced with a heteroatom selected from N, O, or S;

each Z independently is one or more substituents and is selected from the group consisting of H, halo, optionally substituted alkyl, optionally substituted, hydroxyl, carbonyl, $CF_3$, optionally substituted alkenyl, optionally substituted alkynyl, optionally substituted aryl, alkaryl, arylalkyl, optionally substituted heteroaryl, optionally substituted heterocycle, amino, alkylamino, dialkylamino, carboxylic acid, carboxylic ester, carboxamide, nitro, cyano, amide, imide, azide, alkylcarbonyl, optionally substituted acyl, sulfonyl, alkylsulfonyl, sulfinyl, alkylsulfinyl, sulfenyl, alkylsulfenyl, and trialkylammonium; and pharmaceutically acceptable esters, amides, salts, solvates, prodrugs, and enantiomers thereof.

5. The pharmaceutical composition of claim 4, wherein the enzyme inhibiting compound has the structure of Formula (23)

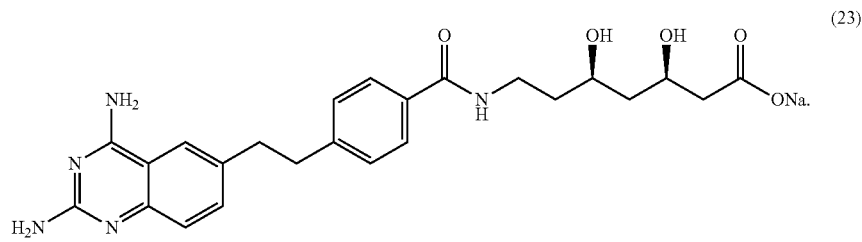
(23)
6. The pharmaceutical composition of claim 4, wherein the enzyme inhibiting compound has the structure of Formula (24)
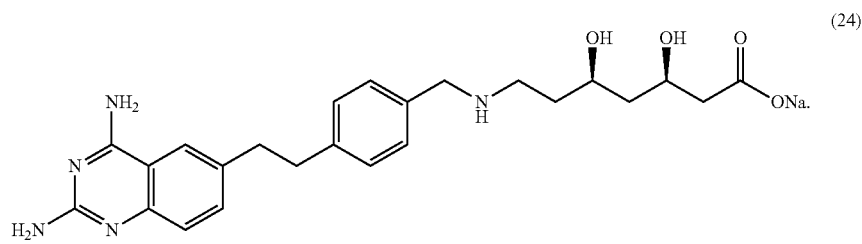
(24)
* * * * *

UNITED STATES PATENT AND TRADEMARK OFFICE
CERTIFICATE OF CORRECTION

PATENT NO. : 8,530,653 B2
APPLICATION NO. : 12/939556
DATED : September 10, 2013
INVENTOR(S) : Michael J. Roberts Page 1 of 1

It is certified that error appears in the above-identified patent and that said Letters Patent is hereby corrected as shown below:

In the Specification

In Column 12, Line 55, the chemical structure (Formula 5) should read

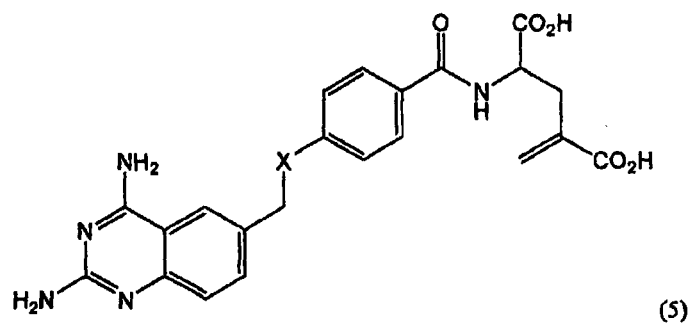

(5)

Signed and Sealed this
Fifteenth Day of July, 2014

Michelle K. Lee
*Deputy Director of the United States Patent and Trademark Office*